(12) United States Patent
Weinschenk et al.

(10) Patent No.: US 10,383,931 B2
(45) Date of Patent: Aug. 20, 2019

(54) PEPTIDES AND COMBINATION OF PEPTIDES FOR USE IN IMMUNOTHERAPY AGAINST CANCERS

(71) Applicant: IMMATICS BIOTECHNOLOGIES GMBH, Tübingen (DE)

(72) Inventors: Toni Weinschenk, Aichwald (DE); Oliver Schoor, Tübingen (DE); Andrea Mahr, Tübingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/138,655

(22) Filed: Sep. 21, 2018

(65) Prior Publication Data

US 2019/0008937 A1 Jan. 10, 2019

Related U.S. Application Data

(63) Continuation of application No. 15/458,893, filed on Mar. 14, 2017.

(60) Provisional application No. 62/309,107, filed on Mar. 16, 2016.

(30) Foreign Application Priority Data

Mar. 16, 2016 (GB) .................................. 1604490.1

(51) Int. Cl.
| | |
|---|---|
| *A61K 39/00* | (2006.01) |
| *G16B 25/00* | (2019.01) |
| *C07K 14/47* | (2006.01) |
| *C07K 14/725* | (2006.01) |
| *C07K 16/18* | (2006.01) |
| *C07K 16/28* | (2006.01) |
| *C12N 5/0783* | (2010.01) |
| *C12N 15/115* | (2010.01) |
| *C12Q 1/6886* | (2018.01) |
| *G01N 33/574* | (2006.01) |
| *G01N 33/68* | (2006.01) |
| *C07K 14/64* | (2006.01) |
| *C07K 14/705* | (2006.01) |
| *C07K 16/00* | (2006.01) |

(52) U.S. Cl.
CPC ...... *A61K 39/0011* (2013.01); *C07K 14/4743* (2013.01); *C07K 14/64* (2013.01); *C07K 14/7051* (2013.01); *C07K 14/70503* (2013.01); *C07K 16/00* (2013.01); *C07K 16/18* (2013.01); *C07K 16/2809* (2013.01); *C12N 5/0638* (2013.01); *C12N 15/115* (2013.01); *C12Q 1/6886* (2013.01); *G01N 33/57484* (2013.01); *G01N 33/6872* (2013.01); *G16B 25/00* (2019.02); *A61K 2039/5158* (2013.01); *A61K 2039/572* (2013.01); *C07K 2319/40* (2013.01); *C12N 2310/16* (2013.01); *C12Q 2600/136* (2013.01); *G01N 2333/70539* (2013.01)

(58) Field of Classification Search
CPC .................................................. C07K 14/4748
See application file for complete search history.

(56) References Cited

U.S. PATENT DOCUMENTS

| | | | |
|---|---|---|---|
| 7,919,467 B2 * | 4/2011 | Ramakrishna | A61K 38/19 514/19.3 |
| 8,119,139 B2 * | 2/2012 | Weinschenk | A61K 39/0011 424/185.1 |
| 9,931,388 B2 * | 4/2018 | Mahr | A61K 35/17 |
| 2003/0138438 A1 | 7/2003 | Mericle et al. | |
| 2011/0229504 A1 | 9/2011 | Fritsche et al. | |
| 2012/0070461 A1 | 3/2012 | Singh et al. | |
| 2012/0308590 A1 | 12/2012 | Yasuharu et al. | |

FOREIGN PATENT DOCUMENTS

| | | |
|---|---|---|
| EP | 2172211 A1 | 4/2010 |
| WO | 2001/075067 A2 | 10/2001 |
| WO | 2007/150077 A2 | 12/2007 |
| WO | 2015/063302 A2 | 5/2015 |
| WO | 2015/187040 A1 | 12/2015 |
| WO | 2016/156230 A1 | 10/2016 |

OTHER PUBLICATIONS

Search Report of British Patent Application No. 1604490.1 dated Dec. 16, 2016.

(Continued)

*Primary Examiner* — Sheela J. Huff
(74) *Attorney, Agent, or Firm* — McBee Moore Woodward & Vanik IP, LLC

(57) ABSTRACT

The present description relates to peptides, proteins, nucleic acids and cells for use in immunotherapeutic methods. In particular, the present description relates to the immunotherapy of cancer. The present description further relates to tumor-associated T-cell peptide epitopes, alone or in combination with other tumor-associated peptides that can for example serve as active pharmaceutical ingredients of vaccine compositions that stimulate anti-tumor immune responses, or to stimulate T-cells ex vivo and transfer into patients. Peptides bound to molecules of the major histocompatibility complex (MHC), or peptides as such, can also be targets of antibodies, soluble T-cell receptors, and other binding molecules.

22 Claims, 6 Drawing Sheets
(6 of 6 Drawing Sheet(s) Filed in Color)
Specification includes a Sequence Listing.

(56) References Cited

OTHER PUBLICATIONS

Dutoit, Valerie et al., "Exploiting the glioblastoma peptidome to discover novel tumour-associated antigens for Immunotherapy", Brain: A Journal of Neurology, Mar. 14, 2012, pp. 1042-1054, vol. 135.

Tomita, Yusuke et al., "Peptides derived from human insulin-like growth factor-II mRNA binding protein 3 can induce human leukocyte antigen-A2-restricted cytotoxic T lymphocytes reactive to cancer cells", Journal of the Japanese Cancer Association, Jan. 2011, pp. 71-78, vol. 102, No. 1.

International Search Report for PCT/EP2017/055973, dated Jul. 12, 2017.

\* cited by examiner

PEPTIDES AND COMBINATION OF PEPTIDES FOR USE IN IMMUNOTHERAPY AGAINST CANCERS

CROSS REFERENCE TO RELATED APPLICATIONS

This application is a Continuation of U.S. application Ser. No. 15/458,893, filed 14 Mar. 2017, which claims the benefit of U.S. Provisional Application Ser. No. 62/309,107, filed 16 Mar. 2016, and Great Britain Application No. 1604490.1, filed 16 Mar. 2016. The content of each of the aforementioned applications is herein incorporated by reference in their entirety.

This application also is related to PCT/EP2017/055973 filed 14 Mar. 2017, the content of which is incorporated herein by reference in its entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-064002_ST25.txt" created on 19 Sep. 2018, and 2,458 bytes in size) is submitted concurrently with the instant application, and the entire contents of the Sequence Listing are incorporated herein by reference.

FIELD

The present description relates to peptides, proteins, nucleic acids and cells for use in immunotherapeutic methods. In particular, the present description relates to the immunotherapy of cancer. The present description further relates to tumor-associated T-cell peptide epitopes, alone or in combination with other tumor-associated peptides that can for example serve as active pharmaceutical ingredients of vaccine compositions that stimulate anti-tumor immune responses, or to stimulate T-cells ex vivo and transfer into patients. Peptides bound to molecules of the major histocompatibility complex (MHC), or peptides as such, can also be targets of antibodies, soluble T-cell receptors, and other binding molecules. The present description further relates to the use of the above peptides for the generation of specific T-cell receptors (TCRs) binding to tumor-associated antigens (TAAs) for targeting cancer cells, the generation of T-cells expressing same, and methods for treating cancers using same. The novel peptide sequences and their variants derived from HLA class I molecules of human tumor cells can be used in vaccine compositions for eliciting anti-tumor immune responses, or as targets for the development of pharmaceutically/immunologically active compounds and cells. Preferred is a peptide that has the amino acid sequence KIQEILTQV (SEQ ID NO:1).

BACKGROUND OF THE INVENTION

Gastric cancer is a disease in which malignant cells form in the lining of the stomach. Stomach or gastric cancer can develop in any part of the stomach and may spread throughout the stomach and to other organs; particularly the esophagus, lungs and the liver. Stomach cancer is the fourth most common cancer worldwide with 930,000 cases diagnosed in 2002. It is a disease with a high death rate (~800,000 per year) making it the second most common cause of cancer death worldwide after lung cancer. It is more common in men and occurs more often in Asian countries and in developing countries.

It represents roughly 2% (25,500 cases) of all new cancer cases yearly in the United States, but it is more common in other countries. It is the leading cancer type in Korea, with 20.8% of malignant neoplasms. In Japan gastric cancer remains the most common cancer for men. Each year in the United States, about 13,000 men and 8,000 women are diagnosed with stomach cancer. Most are over 70 years old.

Stomach cancer is the fourth most common cancer worldwide, after cancers of the lung, breast, and colon and rectum. Furthermore, stomach cancer remains the second most common cause of death from cancer. The American Cancer Society estimates that in 2007 there were an estimated one million new cases, nearly 70% of them in developing countries, and about 800,000 deaths.

Tremendous geographic variation exists in the incidence of this disease around the world. Rates of the disease are highest in Asia and parts of South America and lowest in North America. The highest death rates are recorded in Chile, Japan, South America, and the former Soviet Union.

Gastric cancer is often diagnosed at an advanced stage, because screening is not performed in most of the world, except in Japan (and in a limited fashion in Korea) where early detection is often achieved. Thus, it continues to pose a major challenge for healthcare professionals. Risk factors for gastric cancer are *Helicobacter pylori* (*H. pylori*) infection, smoking, high salt intake, and other dietary factors. A few gastric cancers (1% to 3%) are associated with inherited gastric cancer predisposition syndromes. E-cadherin mutations occur in approximately 25% of families with an autosomal dominant predisposition to diffuse type gastric cancers. This subset of gastric cancer has been termed hereditary diffuse gastric cancer.12 It may be useful to provide genetic counseling and to consider prophylactic gastrectomy in young, asymptomatic carriers of germ-line truncating The wall of the stomach is made up of 3 layers of tissue: the mucosal (innermost) layer, the muscularis (middle) layer, and the serosal (outermost) layer. Gastric cancer begins in the cells lining the mucosal layer and spreads through the outer layers as it grows. Four types of standard treatment are used. Treatment for gastric cancer may involve surgery, chemotherapy, radiation therapy or chemoradiation. Surgery is the primary treatment for gastric cancer. The goal of surgery is to accomplish a complete resection with negative margins (R0 resection). However, approximately 50% of patients with locoregional gastric cancer cannot undergo an R0 resection. R1 indicates microscopic residual cancer (positive margins); and R2 indicates gross (macroscopic) residual cancer but not distant disease. Patient outcome depends on the initial stage of the cancer at diagnosis (NCCN Clinical Practice Guidelines in Oncology™).

The 5-year survival rate for curative surgical resection ranges from 30-50% for patients with stage II disease and from 10-25% for patients with stage Ill disease. These patients have a high likelihood of local and systemic relapse. Metastasis occurs in 80-90% of individuals with stomach cancer, with a six month survival rate of 65% in those diagnosed in early stages and less than 15% of those diagnosed in late stages.

Gliomas are brain tumors originating from glial cells in the nervous system. Glial cells, commonly called neuroglia or simply glia, are non-neuronal cells that provide support and nutrition, maintain homeostasis, form myelin, and participate in signal transmission in the nervous system. The two most important subgroups of gliomas are astrocytomas and oligodendrogliomas, named according to the normal glial cell type from which they originate (astrocytes or oligodendrocytes, respectively). Belonging to the subgroup of astrocytomas, glioblastoma multiforme (referred to as glioblastoma hereinafter) is the most common malignant brain tumor in adults and accounts for approx. 40% of all malignant brain tumors and approx. 50% of gliomas (CB-TRUS, 2006, www.cbtrus.org). It aggressively invades the central nervous system and is ranked at the highest malignancy level (grade IV) among all gliomas. Although there has been steady progress in their treatment due to improvements in neuroimaging, microsurgery, diverse treatment options, such as temozolomide or radiation, glioblastomas remain incurable (Burton and Prados, 2000). The lethal rate of this brain tumor is very high: the average life expectancy is 9 to 12 months after first diagnosis. The 5-year survival rate during the observation period from 1986 to 1990 was 8.0%. To date, the five-year survival rate following aggressive therapy including gross tumor resection is still less than 10% (Burton and Prados, 2000).

The onset of colorectal cancer is the result of interactions between inherited and environmental factors. In most cases adenomatous polyps appear to be precursors to colorectal tumors; however the transition may take many years. The primary risk factor for colorectal cancer is age, with 90% of cases diagnosed over the age of 50 years. Other risk factors for colorectal cancer according to the American Cancer Society include alcohol consumption, a diet high in fat and/or red meat and an inadequate intake of fruits and vegetables. Incidence continues to rise, especially in areas such as Japan, where the adoption of westernized diets with excess fat and meat intake and a decrease in fiber intake may be to blame. However, incidence rates are rising not as fast as previously which may be due to increasing screening and polyp removal, thus preventing progression of polyps to cancer.

As in most solid tumors, first line treatment is surgery, however, its benefits remain confined to early-stage patients, yet a significant proportion of patients is diagnosed in advanced stages of the disease. For advanced colorectal cancer chemotherapy regimens based on fluorouracil-based regimens are standard of care. The majority of these regimens are the so-called FOLFOX (infusional 5-FU/leucovorin plus oxaliplatin) and FOLFIRI (irinotecan, leucovorin, bolus and continuous-infusion 5-FU) protocols.

The introduction of third-generation cytotoxics such as irinotecan and oxaliplatin has raised the hope of significantly improving efficacy, but prognosis is still relatively poor, and the survival rate generally remains at approximately 20 months in metastatic disease and, as a result, the unmet needs in the disease remain high.

Immunotherapy of cancer represents an option of specific targeting of cancer cells while minimizing side effects. Cancer immunotherapy makes use of the existence of tumor associated antigens.

The current classification of tumor associated antigens (TAAs) can be categorized into the following groups:
a) Cancer-testis antigens: The first TAAs ever identified that can be recognized by T-cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T-cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides. MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997). MHC class II molecules can be found predominantly on professional antigen presenting cells (APCs), and primarily present peptides of exogenous or transmembrane proteins that are taken up by APCs e.g., during endocytosis, and are subsequently processed.

Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. It is well known that the TCR, the peptide and the MHC are thereby present in a stoichiometric amount of 1:1:1.

CD4-positive helper T-cells play an important role in inducing and sustaining effective responses by CD8-positive cytotoxic T-cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T-cell-(CTL-) friendly cytokine milieu (Mortara et al., 2006) and attract effector cells, e.g., CTLs, natural killer (NK) cells, macrophages, and granulocytes.

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006). Elongated (longer) peptides of the description can function as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T-cells are sufficient for inhibiting manifestation of tumors via inhibition of angiogenesis by secretion of interferon-gamma (IFNγ). There is evidence for CD4 T-cells as direct anti-tumor effectors (Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T-cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T-cells bearing specific T-cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e., copy numbers of the respective peptide per cell). Tumor-specific and tumor-associated antigens are often derived from proteins directly involved in transformation of a normal cell to a tumor cell due to their function, e.g., in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Therefore, TAAs are a starting point for the development of a T-cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes overexpressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T-cell with a corresponding TCR has to be present and the immunological tolerance for this particular epitope needs to be absent or minimal. In a very preferred embodiment of the description it is therefore important to select only those over- or selectively presented peptides against which a functional and/or a proliferating T-cell can be found. Such a functional T-cell is defined as a T-cell, which upon stimulation with a specific antigen can be clonally expanded and is able to execute effector functions ("effector T-cell").

In case of targeting peptide-MHC by specific TCRs (e.g., soluble TCRs) and antibodies or other binding molecules (scaffolds) according to the description, the immunogenicity of the underlying peptides is secondary. In these cases, the presentation is the determining factor.

Thus, in view of the above and similar situations in other camcers, there remains a need for new efficacious and safe treatment option for gastric cancer, prostate carcinoma, oral cavity carcinomas, oral squamous carcinoma (OSCC), acute myeloid leukemia (AML), *H. pylori*-induced MALT lymphoma, colon carcinoma/colorectal cancer, glioblastoma, non-small-cell lung cancer (NSCLC), cervical carcinoma, human breast cancer, prostate cancer, colon cancer, pancreatic cancers, pancreatic ductal adenocarcinoma, ovarian cancer, hepatocellular carcinoma, liver cancer, brain tumors of different phenotypes, leukemias such as acute lymphoblastic leukemia (ALL), lung cancer, Ewing's sarcoma, endometrial cancer, head and neck squamous cell carcinoma, epithelial cancer of the larynx, oesophageal carcinoma, oral carcinoma, carcinoma of the urinary bladder, ovarian carcinomas, renal cell carcinoma, atypical meningioma, papillary thyroid carcinoma, brain tumors, salivary duct carcinoma, cervical cancer, extranodal T/NK-cell lymphomas, Non-Hodgkins Lymphoma and malignant solid tumors of the lung and breast and other tumors, optimally enhancing the well-being of the patients without using chemotherapeutic agents or other agents which may lead to severe side effects.

WO 2015/187040 relates to amino sphingoglycolipid analogues and peptide derivatives thereof, compositions comprising these compounds and methods of treating or preventing diseases or conditions using such compounds, especially diseases or conditions relating to cancer, infection, atopic disorders, autoimmune disease or diabetes, KIQEILTQV is SEQ ID NO:377 disclosed as a peptide that contains within its sequence one or more epitopes that bind to MHC molecules and induce T cell responses.

US 2012-0308590 discloses KIQEILTQV (SEQ ID NO:3) as belonging to IMP-3 552-560 (insulin-like growth factor II mRNA binding protein 3) for lung cancer and esophageal cancer treatment. Similarly, Tomita, Y. et al. disclose the peptide as derived from IMP-3.

US 20110142919 discloses KIQEILTQV (SEQ ID NO:409) as derived from Putative RNA binding protein KOC and identified by MS.

Dutoit et al. (2012) disclose KIQEILTQV (NP_006538) for glioblastoma treatment.

WO 2007/150077 discloses immunogenic peptides isolated from ovarian cancer samples. The peptide IGF2BP3-001 is SEQ ID No: 158.

BRIEF SUMMARY OF THE INVENTION

In an aspect, the present description relates to a peptide comprising an amino acid sequence consisting of SEQ ID NO:1 or a variant sequence thereof which is at least 65%, preferably at least 77%, and more preferably at least 85% homologous (preferably at least 75% or at least 85% identical) to SEQ ID NO:1, wherein said variant binds to MHC and/or induces T-cells cross-reacting with said peptide, or a pharmaceutically acceptable salt thereof, and wherein said peptide is not the underlying full-length polypeptide. Furthermore, said peptide is not an IMP-3 and/or KOC-derived antigen.

The present description further relates to a peptide of the present description comprising a sequence consisting of SEQ ID NO:1 or a variant thereof, which is at least 65%, preferably at least 75%, and more preferably at least 85% homologous (preferably at least 75% or at least 85% identical) to SEQ ID NO:1, wherein said peptide or variant thereof has an overall length of between 8 and 100, preferably between 8 and 30, and most preferably of between 8 and 14 amino acids, wherein said peptide or variant binds to MHC and/or induces T-cells cross-reacting with said peptide, or a pharmaceutically acceptable salt thereof.

The peptide according to the present description, is the peptide according to SEQ ID NO: 1, KIQEILTQV as well as variants thereof as described herein.

The present description furthermore generally relates to the peptides according to the present description for use in the treatment of proliferative diseases, such as gastric cancer, prostate carcinoma, oral cavity carcinomas, oral squamous carcinoma (OSCC), acute myeloid leukemia (AML), *H. pylori*-induced MALT lymphoma, colon carcinoma/colorectal cancer, glioblastoma, non-small-cell lung cancer (NSCLC), cervical carcinoma, human breast cancer, prostate cancer, colon cancer, pancreatic cancers, pancreatic ductal adenocarcinoma, ovarian cancer, hepatocellular carcinoma, liver cancer, brain tumors of different phenotypes, leukemias such as acute lymphoblastic leukemia (ALL), lung cancer, Ewing's sarcoma, endometrial cancer, head and neck squamous cell carcinoma, epithelial cancer of the larynx, oesophageal carcinoma, oral carcinoma, carcinoma of the urinary bladder, ovarian carcinomas, renal cell carcinoma, atypical meningioma, papillary thyroid carcinoma, brain tumors, salivary duct carcinoma, cervical cancer, extranodal T/NK-cell lymphomas, Non-Hodgkins Lymphoma and malignant solid tumors of the lung and breast and other tumors.

Preferrd is the use in non-small cell lung cancer, small cell lung cancer, renal cell cancer, brain cancer (e.g., glioblastoma, neuroblastoma), gastric cancer, colorectal cancer, hepatocellular cancer, head and neck cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer. More preferred is the use in pancreatic cancer, hepatocellular cancer, gastric cancer, and/or colorectal cancer.

Particularly preferred is the peptide—alone or in combination—according to the present description consisting of SEQ ID NO:1. More preferred is the peptide—alone or in combination—consisting of SEQ ID NO:1, and their uses in the immunotherapy of gastric cancer, prostate carcinoma, oral cavity carcinomas, oral squamous carcinoma (OSCC), acute myeloid leukemia (AML), *H. pylori*-induced MALT lymphoma, colon carcinoma/colorectal cancer, glioblastoma, non-small-cell lung cancer (NSCLC), cervical carcinoma, human breast cancer, prostate cancer, colon cancer, pancreatic cancers, pancreatic ductal adenocarcinoma, ovarian cancer, hepatocellular carcinoma, liver cancer, brain tumors of different phenotypes, leukemias such as acute lymphoblastic leukemia (ALL), lung cancer, Ewing's sarcoma, endometrial cancer, head and neck squamous cell carcinoma, epithelial cancer of the larynx, oesophageal carcinoma, oral carcinoma, carcinoma of the urinary bladder, ovarian carcinomas, renal cell carcinoma, atypical meningioma, papillary thyroid carcinoma, brain tumors, salivary duct carcinoma, cervical cancer, extranodal T/NK-cell lymphomas, Non-Hodgkins Lymphoma and malignant solid tumors of the lung and breast and other tumors.

The IGF2BP1 gene encodes a member of the insulin-like growth factor 2 mRNA-binding protein family. The protein encoded by this gene contains four K homology domains and two RNA recognition motifs. It functions by binding to the mRNAs of certain genes, including insulin-like growth factor 2, beta-actin and beta-transducin repeat-containing protein, and regulating their translation. Two transcript variants encoding different isoforms have been found for this gene. The IGF2BP1 gene maps to chromosome 17q21.32. A 580 kb microdeletion in this locus is associated with mental retardation, microcephaly, cleft palate and cardiac malformation (Rooryck et al., 2008).

IGF2BP1 is over-expressed in a large variety of different cancer entities. In breast cancer, moderate (30%) and high (5%) IGF2BP1 gene amplification as well as amplification-independent over-expression of IGF2BP1 has been detected (Doyle et al., 2000; Ioannidis et al., 2003). The colorectal cancer study, performed by Ross and colleagues, revealed IGF2BP1 over-expressed in the majority of colorectal cancer specimens (81%), whereas it was scarce or absent from normal colon tissue (Ross et al., 2001). Ioannidis and colleagues provide evidence for IGF2BP1 expression in a panel of cancer types, including colon cancer (1/1), prostate cancer (1/4), breast cancer (3/4), different sarcoma (24/33), monomyelocytic leukemia (1/2), 12/24 malignant neuroepithelial tumors, 2/5 benign neuroepithelial tumors and 4/15 non-small cell lung carcinomas (Ioannidis et al., 2001; Ioannidis et al., 2004). Furthermore, IGF2BP1 was shown to be over-expressed in adenocarcinoma and low malignant potential tumors of the ovary (Gu et al., 2004) and ovarian serous carcinoma effusions (Davidson et al., 2014) as well as in hepatocellular cancer (2/7 patients) (Himoto et al., 2005; Gutschner et al., 2014), choriocarcinoma (Hsieh et al., 2013), neuroblastoma (Bell et al., 2015) and rhabdomyosarcoma (Faye et al., 2015). Up-regulation of IGF2BP1 expression has further been described in different testicular neoplasias, like pre-invasive testicular carcinoma in situ, classical and spermatocytic seminoma and undifferentiated embryonal carcinoma (Hammer et al., 2005). In acute lymphoblastic leukemia, IGF2BP1 over-expression appears to be characteristic for the subgroup of ETC6/RUNX1-positive tumors (Stoskus et al., 2011). In malignant melanoma, increased expression of IGF2BP1 was shown to be associated with over-activity of the Wnt/beta-catenin signaling pathway (Elcheva et al., 2008). IGF2BP2 over-expression in basal cell carcinoma correlates with activation of Wnt as well as Hedgehog signaling (Noubissi et al., 2014).

High IGF2BP1 levels appear to be associated with poor prognosis in different cancer entities. IGF2BP1 over-expression was shown to be significantly correlated with reduced recurrence free and overall survival in ovarian cancer patients (Gu et al., 2004; Kobel et al., 2007). Furthermore, positive immunostaining of IGF2BP1 correlated with tumor size, non-well-differentiated tumor grade and poor prognosis in patients with lung cancer (Kato et al., 2007). In colorectal cancer, IGF2BP1 expression was found to be associated with increased metastasis formation and recurrence as well as with shorter survival times (Dimitriadis et al., 2007). Over-expression of IGF2BP1 is associated with poor prognosis in hepatocellular cancer (Zhou et al., 2015b) and with lower overall patient survival in neuroblastoma (Bell et al., 2015). IGF2BP1 hyper-methylation was shown to be associated with an aggressive disease phenotype in meningioma (Vengoechea et al., 2013).

IGF2BP1 expression was shown to be associated with advanced disease stages in ovarian cancer, colorectal cancer and neuroblastoma. Koebel and colleagues report preferential detection of high IGF2BP1 expression levels in high-grade and late stage ovarian cancer specimens (Kobel et al., 2007). In colorectal cancer, frequency and intensity of IGF2BP1 staining were shown to increase with progression of the disease to lymph node metastases. High levels of IGF2BP1 protein were detected in 97% of colorectal cancer lymph node metastases and the expression level in primary cancers correlated well with the presence of lymph node metastases (Vainer et al., 2008). In neuroblastoma, IGF2BP1 expression was associated with stage 4 cancers (Bell et al., 2015).

The present description furthermore relates to peptides according to the present description that have the ability to bind to a molecule of the human major histocompatibility complex (MHC) class-I or—in an elongated (longer) form, such as a length-variant—MHC class-II.

The present description further relates to the peptides according to the present description wherein said peptides (each) comprise, consist of, or consist essentially of an amino acid sequence according to SEQ ID NO:1.

The present description further relates to the peptides according to the present description, wherein said peptide is modified and/or includes non-peptide bonds.

The present description further relates to the peptides according to the present description, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present description further relates to a nucleic acid, encoding the peptides according to the present description. The present description further relates to the nucleic acid according to the present description that is DNA, cDNA, PNA, RNA or combinations thereof.

The present description further relates to an expression vector capable of expressing and/or expressing a nucleic acid according to the present description.

The present description further relates to a peptide according to the present description, a nucleic acid according to the present description or an expression vector according to the present description for use in the treatment of diseases and in medicine, in particular in the treatment of cancer.

The present description further relates to antibodies that are specific against the peptides according to the present description or complexes of said peptides according to the present description with MHC, and methods of making these.

The present description further relates to a host cell comprising a nucleic acid according to the present description or an expression vector as described before.

The present description further relates to the host cell according to the present description that is an antigen presenting cell, and preferably is a dendritic cell.

The present description further relates to a method for producing a peptide according to the present description, said method comprising culturing the host cell according to the present description, and isolating the peptide from said host cell or its culture medium.

The present description further relates to said method according to the present description, wherein the antigen is loaded onto class I or II MHC molecules expressed on the surface of a suitable antigen-presenting cell or artificial antigen-presenting cell by contacting a sufficient amount of the antigen with an antigen-presenting cell.

The present description further relates to the method according to the present description, wherein the antigen-presenting cell comprises an expression vector capable of expressing and/or expressing said peptide containing SEQ ID NO:1, preferably containing SEQ ID NO:1, or a variant amino acid sequence.

The present description further relates to activated T-cells, produced by the method according to the present description, wherein said T-cell selectively recognizes a cell which expresses a polypeptide comprising an amino acid sequence according to the present description.

The present description further relates to a method of killing target-cells in a patient which target-cells aberrantly express a polypeptide comprising any amino acid sequence according to the present description, the method comprising administering to the patient an effective number of T-cells as produced according to the present description.

The present description further relates to the use of any peptide as described, the nucleic acid according to the present description, the expression vector according to the present description, the cell according to the present description, the activated T lymphocyte, the T-cell receptor or the antibody or other peptide- and/or peptide-MHC-binding molecules according to the present description as a medicament or in the manufacture of a medicament. Preferably, said medicament is active against cancer.

Preferably, said medicament is a cellular therapy, a vaccine or a protein based on a soluble TCR or antibody.

The present description further relates to a use according to the present description, wherein said cancer cells are from gastric cancer, prostate carcinoma, oral cavity carcinomas, oral squamous carcinoma (OSCC), acute myeloid leukemia (AML), H. pylori-induced MALT lymphoma, colon carcinoma/colorectal cancer, glioblastoma, non-small-cell lung cancer (NSCLC), cervical carcinoma, human breast cancer, prostate cancer, colon cancer, pancreatic cancers, pancreatic ductal adenocarcinoma, ovarian cancer, hepatocellular carcinoma, liver cancer, brain tumors of different phenotypes, leukemias such as acute lymphoblastic leukemia (ALL), lung cancer, Ewing's sarcoma, endometrial cancer, head and neck squamous cell carcinoma, epithelial cancer of the larynx, oesophageal carcinoma, oral carcinoma, carcinoma of the urinary bladder, ovarian carcinomas, renal cell carcinoma, atypical meningioma, papillary thyroid carcinoma, brain tumors, salivary duct carcinoma, cervical cancer, extranodal T/NK-cell lymphomas, Non-Hodgkins Lymphoma and malignant solid tumors of the lung and breast and other tumors.

The present description further relates to biomarkers based on the peptides according to the present description, herein called "targets," that can be used in the diagnosis of cancer, preferably non-small cell lung cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC. Optionally the antibody carries a further effector function such as an immune stimulating domain or toxin.

The present description further relates to the use of these novel targets for the identification of TCRs that recognize at least one of said targets, and preferably the identification of said TCRs that activate T-cells.

The present description also relates to the use of these novel targets in the context of cancer treatment.

The present description further relates to the use of the peptides according to the invention for the production of TCRs, individual TCR subunits (alone or in combination), and subdomains thereof, in particular soluble TCR (sTCRs) and cloned TCRs, said TCRs engineered into autologous or allogeneic T-cells, and methods of making same, as well as other cells bearing said TCR or cross-reacting with said TCRs.

The present description further relates to a TCR protein, individual TCR subunits (alone or in combination), and subdomains thereof, in particular soluble TCR (sTCRs) and cloned TCRs that bind to a KIQEILTQV (SEQ ID NO:1)-HLA-A*02 complex comprising a TCR alpha chain variable domain and a TCR beta chain variable domain.

The present description further relates to an isolated nucleic acid comprising a nucleotide sequence encoding a TCR of the present description. The present description further relates to a recombinant expression vector comprising a nucleic acid encoding a TCR alpha chain, beta chain, or both, as produced according to the present description.

The present description further relates to an isolated host cell comprising the recombinant expression vector expressing the nucleic acid encoding the TCR alpha chain, beta chain, or both, of the present description.

The present description further relates to an isolated host cell comprising the recombinant expression vector of the present description, preferably wherein the cell is a peripheral blood lymphocyte (PBL).

The present description further relates to an isolated PBL comprising the recombinant expression vector of the present description, wherein the PBL is a CD8+ T-cell or a CD4+ T-cell.

The present description further relates to a population of cells comprising at least one host cell of the present description.

The present description further relates to TCR proteins of the present description for use in the treatment of proliferative diseases, such as, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "T-cell response" means the specific proliferation and activation of effector functions induced by a peptide in vitro or in vivo. For MHC class I restricted cytotoxic T-cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, or 12 or longer, and in case of MHC class II peptides (elongated variants of the peptides of the description) they can be as long as 13, 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present description differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the description, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the description as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present description), if it is capable of inducing an immune response. In the case of the present description, immunogenicity is more specifically defined as the ability to induce a T-cell response. Thus, an "immunogen" would be a molecule that is capable of inducing an immune response, and in the case of the present description, a molecule capable of inducing a T-cell response. In another aspect, the immunogen can be the peptide, the complex of the peptide with MHC, oligopeptide, and/or protein that is used to raise specific antibodies or TCRs against it.

A class I T-cell "epitope" requires a short peptide that is bound to a class I MHC receptor, forming a ternary complex (MHC class I alpha chain, beta-2-microglobulin, and peptide) that can be recognized by a T-cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 1

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

In an embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this description are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein the term "a nucleotide coding for (or encoding) a TCR protein" refers to a nucleotide sequence coding for the TCR protein including artificial (man-made) start and stop codons compatible for the biological system the sequence is to be expressed by, for example, T-cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. In an aspect, such polynucleotides are part of a vector and/or such polynucleotides or polypeptides are part of a composition, and still be isolated in that such vector or composition is not part of its natural environment.

The polynucleotides, and recombinant or immunogenic polypeptides, disclosed in accordance with the present description may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present description, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present description can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present description, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference and
(iv) the alignment has to start at position 1 of the aligned sequences;
and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present description thus provides a peptide comprising a sequence that is selected from the group of consisting of SEQ ID NO:1 to SEQ ID NO:10 or a variant thereof which is 85% homologous to SEQ ID NO:1 to SEQ ID NO:10, or a variant thereof that will induce T-cells cross-reacting with said peptide. The peptides of the description have the ability to bind to a molecule of the human major histocompatibility complex (MHC) class-I or elongated versions of said peptides to class II.

In the present description, the term "homologous" refers to the degree of identity (see percent identity above) between sequences of two amino acid sequences, i.e., peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T-cells induced by a variant of a specific peptide will be able to cross-react with the peptide itself (Appay et al., 2006; Colombetti et al., 2006).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence consisting of SEQ ID NO:1. Preferred is KIQEILTQV (SEQ ID NO:1). For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T-cells. Similarly, a TCR protein may be modified so that it at least maintains, if not improves, the ability to interact with and bind to a suitable MHC molecule/KIQEILTQV (SEQ ID NO:1) complex, such as HLA-A*02 or -DR, and in that way it at least maintains, if not improves, the ability to activate T-cells.

These T-cells can subsequently cross-react with cells and kill cells that express a polypeptide that contains the natural amino acid sequence of the cognate peptide, such as KIQEILTQV (SEQ ID NO:1), as defined in the aspects of the description. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequence set forth in SEQ ID NO:1, by maintaining the known anchor residues, and would be able to determine whether such variants maintain the ability to bind MHC class I or II molecules/KIQEILTQV (SEQ ID NO:1) complexes. The variants of the present description retain the ability to bind MHC class I or II molecules/KIQEILTQV (SEQ ID NO:1) complexes. T-cells expressing the variants of the present description can subsequently kill cells that express a polypeptide containing the natural amino acid sequence of the cognate peptide, such as KIQEILTQV (SEQ ID NO:1).

The original (unmodified) peptides or TCR proteins as disclosed herein can be modified by the substitution of one or more residues at different, possibly selective, sites within the peptide chain, if not otherwise stated. Preferably those substitutions are located at the end of the amino acid chain of said peptide. For TCR proteins, preferably those substitutions are located at variable domains of TCR alpha chain and TCR beta chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the description and yet still be encompassed by the disclosure herein.

In addition, non-standard amino acids (i.e., other than the common naturally occurring proteinogenic amino acids) may also be used for substitution purposes to produce immunogens and immunogenic polypeptides according to the present description.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or —II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the TCR can be modified by replacement with other amino acids whose incorporation do not substantially affect T-cell reactivity and does not eliminate binding to the relevant MHC. Thus, apart from the proviso given, the peptide of the description may be any peptide (by which term the inventors include oligopeptide or polypeptide), which includes the amino acid sequences or a portion or variant thereof as given.

TABLE 2

Variants of the peptide of the invention

| | Position: | | | | | | | | |
|---|---|---|---|---|---|---|---|---|---|
| | 1 | 2 | 3 | 4 | 5 | 6 | 7 | 8 | 9 |
| IGF2BP3-001 (SEQ ID NO: 1) | K | I | Q | E | I | L | T | Q | V |
| IGF2BP3-001 A1 (SEQ ID NO: 2) | A | I | Q | E | I | L | T | Q | V |
| IGF2BP3-001 A2 (SEQ ID NO: 3) | K | A | Q | E | I | L | T | Q | V |
| IGF2BP3-001 A3 (SEQ ID NO: 4) | K | I | A | E | I | L | T | Q | V |
| IGF2BP3-001 A4 (SEQ ID NO: 5) | K | I | Q | A | I | L | T | Q | V |
| IGF2BP3-001 A5 (SEQ ID NO: 6) | K | I | Q | E | A | L | T | Q | V |
| IGF2BP3-001 A6 (SEQ ID NO: 7) | K | I | Q | E | I | A | T | Q | V |
| IGF2BP3-001 A7 (SEQ ID NO: 8) | K | I | Q | E | I | L | A | Q | V |
| IGF2BP3-001 A8 (SEQ ID NO: 9) | K | I | Q | E | I | L | T | A | V |
| IGF2BP3-001 A9 (SEQ ID NO: 10) | K | I | Q | E | I | L | T | Q | A |

Longer (elongated) peptides may also be suitable. It is possible that MHC class I epitopes, although usually the actual epitope are residues that do not substantially affect proteolytic cleavage necessary to expose the actual epitope during processing.

The peptides of the description can be elongated by up to four amino acids, that is 1, 2, 3 or 4 amino acids can be added to either end in any combination between 8 and 11 amino acids long, are generated by peptide processing from longer peptides or proteins that include the actual epitope. It is preferred that the residues that flank between 4:0 and 0:4. Combinations of the elongations according to the description can be found in Table 3.

TABLE 3

Combinations of the elongations of peptides of the description

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |
| N-terminus | C-terminus |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present description may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present description provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present description will have the ability to bind to a molecule of the human major histocompatibility complex (MHC) class I or II. Binding of a peptide or a variant to a MHC complex may be tested by methods known in the art.

Preferably, when the T-cells specific for a peptide according to the present description are tested against the substituted peptides, the peptide concentration at which the substituted peptides achieve half the maximal increase in lysis relative to background is no more than about 1 mM, preferably no more than about 1 μM, more preferably no more than about 1 nM, and still more preferably no more than about 100 pM, and most preferably no more than about 10 pM. It is also preferred that the substituted peptide be recognized by T-cells from more than one individual, at least two, and more preferably three individuals.

Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens (Aleksic et al. 2012; Kunert et al. 2013). It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance (Xing et al. 2012; Ruella et al. 2014; Sharpe et al. 2015), meaning that only T-cells with low-affinity TCRs for self antigens remain. Therefore, affinity of TCRs or variants of the present description to MAG-003 have been enhanced by methods well known in the art as described below.

A "pharmaceutical composition" is a composition suitable for administration to a human being in a medical setting. Preferably, a pharmaceutical composition is sterile and produced according to GMP guidelines.

The pharmaceutical compositions comprise the peptides or TCR proteins either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral—NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like.

Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

Another embodiment of the present invention relates to a non-naturally occurring peptide wherein said peptide consists or consists essentially of an amino acid sequence according to SEQ ID No: 1 to SEQ ID No: 10 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, KCl, KBr, $KNO_3$, $KClO_4$, KI, KSCN, $Na_3PO_4$, $Na_2HPO_4$, $NaH_2PO_4$, $Na_2SO_4$, $NaCH_3COO$, NaCl, NaBr, $NaNO_3$, $NaClO_4$, NaI, NaSCN, $ZnCl_2$ $Cs_3PO_4$, $Cs_2HPO_4$, $CsH_2PO_4$, $Cs_2SO_4$, $CsCH_3COO$, CsCl, CsBr, $CsNO_3$, $CsClO_4$, CsI, CsSCN, $Li_3PO_4$, $Li_2HPO_4$, $LiH_2PO_4$, $Li_2SO_4$, $LiCH_3COO$, LiCl, LiBr, $LiNO_3$, $LiClO_4$, LiI, LiSCN, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)$, $Ca_2HPO_4$, $Ca(H_2PO_4)_2$, $CaSO_4$, $Ca(CH_3COO)_2$, $CaCl_2)$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, Bale, and $Ba(SCN)_2$. Particularly preferred are NH acetate, $MgCl_2$, $KH_2PO_4$, $Na_2SO_4$, KCl, NaCl, and $CaCl_2)$, such as, for example, the chloride or acetate (trifluoroacetate) salts.

In an especially preferred embodiment, the pharmaceutical compositions comprise the peptides or TCR proteins as salts of acetic acid (acetates), trifluoro acetates or hydrochloric acid (chlorides).

A further aspect of the description provides a nucleic acid (for example a polynucleotide) encoding a peptide or peptide variant and a TCR protein and TCR variants of the description. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the description provides an expression vector capable of expressing a polypeptide according to the description.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the description employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the description. Thus, the DNA encoding the peptide or variant of the description may be used in accordance with known techniques, appropriately modified in view of the teachings contained herein, to construct an expression vector, which is then used to transform an appropriate host cell for the expression and production of the polypeptide of the description. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the description may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the description are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), planT-cells, animal cells and insecT-cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potenT-cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the description are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present description also relates to a host cell transformed with a polynucleotide vector construct of the present description. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insecT-cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present description is accomplished by well-known methods that typically depend on the type of vector used. With regard to transformation of prokaryotic host cells, see, for example, Cohen et al. (Cohen et al., 1972) and (Green and Sambrook, 2012). Transformation of yeasT-cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeasT-cell, bacterial cells, insecT-cells and vertebrate cells.

Successfully transformed cells, i.e., cells that contain a DNA construct of the present description, can be identified by well-known techniques such as PCR. Alternatively, the presence of the protein in the supernatant can be detected using antibodies.

It will be appreciated that certain host cells of the description are useful in the preparation of the peptides of the description, for example bacterial, yeast and insecT-cells. However, other host cells may be useful in certain therapeutic methods. For example, antigen-presenting cells, such as dendritic cells, may usefully be used to express the peptides of the description such that they may be loaded into appropriate MHC molecules. Thus, the current description provides a host cell comprising a nucleic acid or an expression vector according to the description.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the description provides a method of producing a peptide or its variant, the method comprising culturing a host cell and isolating the peptide from the host cell or its culture medium.

In another embodiment the TCR proteins, the nucleic acid or the expression vector of the description are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g., between 50 μg and 1.5 mg, preferably 125 μg to 500 μg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g., Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T-cells for the respective opposite CDR as noted above.

The medicament of the description may also include one or more adjuvants. Adjuvants are substances that non-specifically enhance or potentiate the immune response (e.g., immune responses mediated by CD8-positive T-cells and helper-T (TH) cells to an antigen, and would thus be considered useful in the medicament of the present description. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present description. Other TLR binding molecules such as RNA binding TLR 7, TLR 8 and/or TLR 9 may also be used.

Other examples for useful adjuvants include, but are not limited to chemically modified CpGs (e.g., CpR, Idera), dsRNA analogues such as Poly(I:C) and derivates thereof (e.g., AmpliGen®, Hiltonal®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g., anti-CD40, anti-TGFbeta, anti-TNFalpha receptor) and SC58175, which may act therapeutically and/or as an adjuvant. The amounts and concentrations of adjuvants and additives useful in the context of the present description can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the description the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the description the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the description, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomateous or cancerous diseases. Exemplary formulations can be found in, for example, EP2112253.

It is important to realize that the immune response triggered by the vaccine according to the description attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g., antigenic) determinant. In one embodiment, a scaffold is able to direct the entity to which it is attached (e.g., a (second) antigen binding moiety) to a target site, for example to a specific type of tumor cell or tumor stroma bearing the antigenic determinant (e.g., the complex of a peptide with MHC, according to the application at hand). In another embodiment a scaffold is able to activate signaling through its target antigen, for example a T-cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T-cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e., not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labeling which provides that the bound scaffold can be detected by determining the presence or absence of a signal provided by the label. For example, the scaffold can be labeled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present description further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. In an aspect, at least one or more aptamers are taken up by tumor cells and thus can function as molecular vehicles for the targeted delivery of anti-cancer agents such as siRNA into tumor cells.

Aptamers can be selected against complex targets such as cells and tissues and complexes of the peptides according to the description at hand with the MHC molecule, using the cell-SELEX (Systematic Evolution of Ligands by Exponential enrichment) technique.

The peptides of the present description can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the description to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the description to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present description are all explicitly incorporated by reference in their entireties.

Preferably, the antibody is binding with a binding affinity of below 20 nanomolar, preferably of below 10 nanomolar, to the complex, which is also regarded as "specific" in the context of the present description.

The present description relates to a TCR protein or a variant or functional fragment thereof that specifically binds to SEQ ID NO:1.

The present description further relates to the TCR protein according to the description, wherein the TCR protein is (chemically) modified and/or includes non-peptide bonds.

The present description further relates to a nucleic acid, encoding the TCR proteins according to the description, provided that the TCR protein is not the complete (full) human protein.

The present description further relates to the nucleic acid according to the description that is DNA, cDNA, PNA, RNA or combinations thereof.

The present description further relates to an expression vector capable of expressing a nucleic acid according to the present description.

The present description further relates to a TCR protein according to the present description, a nucleic acid according to the present description or an expression vector according to the present description for use in medicine, in particular in the (improved) treatment of gastric cancer, colorectal cancer and/or glioblastoma.

The present description further relates to a host cell comprising a nucleic acid according to the description or an expression vector according to the description.

The present description further relates to the host cell according to the present description that is a T-cell, and preferably a CD8-positive T-cell or CD4-positive T-cell.

The present description further relates to a method of producing a TCR protein according to the present description, said method comprising incubating PBMCs from HLA-A*02-negative healthy donors with A2/IGF2BP3-001 (SEQ ID NO:1) monomers, incubating the PBMCs with tetramer-phycoerythrin (PE) and isolating the high avidity T-cells by fluorescence activated cell sorting (FACS)-Calibur analysis.

The present description further relates to a method of producing a TCR protein according to the present description, said method comprising incubating PBMCs from HLA-A*02-negative healthy donors with A2/p286-1Y2L monomers, incubating the PBMCs with tetramer-phycoerythrin (PE) and isolating the high avidity T-cells by fluorescence activated cell sorting (FACS)-Calibur analysis.

The present description further relates to a method of producing a TCR protein according to the present description, said method comprising incubating PBMCs from HLA-A*02-negative healthy donors with A2/p286-1Y2L9L monomers, incubating the PBMCs with tetramer-phycoerythrin (PE) and isolating the high avidity T-cells by fluorescence activated cell sorting (FACS)-Calibur analysis.

The present description further relates to a method of producing a TCR protein according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with IGF2BP3-001, incubating PBMCs obtained from the transgenic mice with tetramer-phycoerythrin (PE), and isolating the high avidity T-cells by fluorescence activated cell sorting (FACS)-Calibur analysis.

The present description further relates to a method of producing a TCR protein according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with p286-1Y2L, incubating PBMCs obtained from the transgenic mice with tetramer-phycoerythrin (PE), and isolating the high avidity T-cells by fluorescence activated cell sorting (FACS)-Calibur analysis.

The present description further relates to a method of producing a TCR protein according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with p286-1Y2L9L, incubating PBMCs obtained from the transgenic mice with tetramer-phycoerythrin (PE), and isolating the high avidity T-cells by fluorescence activated cell sorting (FACS)-Calibur analysis.

The present description further relates to a method of killing target cells in a patient which target cells aberrantly express IGF2BP3-001, the method comprising administering to the patient an effective number of T-cells as according to the present description.

The present description further relates to the use of any TCR protein described, a nucleic acid according to the present description, an expression vector according to the present description, a cell according to the present description, or an activated cytotoxic T lymphocyte according to the present description as a medicament or in the manufacture of a medicament. The present description further relates to a use according to the present description, wherein the medicament is active against cancer.

The present description further relates to a use according to the description, wherein said cancer cell is selected from gastric cancer, prostate carcinoma, oral cavity carcinomas, oral squamous carcinoma (OSCC), acute myeloid leukemia (AML), H. pylori-induced MALT lymphoma, colon carcinoma/colorectal cancer, glioblastoma, non-small-cell lung cancer (NSCLC), cervical carcinoma, human breast cancer, prostate cancer, colon cancer, pancreatic cancers, pancreatic ductal adenocarcinoma, ovarian cancer, hepatocellular carcinoma, liver cancer, brain tumors of different phenotypes, leukemias such as acute lymphoblastic leukemia (ALL), lung cancer, Ewing's sarcoma, endometrial cancer, head and neck squamous cell carcinoma, epithelial cancer of the larynx, oesophageal carcinoma, oral carcinoma, carcinoma of the urinary bladder, ovarian carcinomas, renal cell carcinoma, atypical meningioma, papillary thyroid carcinoma, brain tumors, salivary duct carcinoma, cervical cancer, extranodal T/NK-cell lymphomas, Non-Hodgkins Lymphoma and malignant solid tumors of the lung and breast and other tumors.

The present description further relates to particular marker proteins and biomarkers based on the peptides according to the present description, herein called "targets" that can be used in the diagnosis and/or prognosis of the camcers as above, in particular gastric cancer, colorectal cancer and glioblastoma. The present description also relates to the preferred use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g., CDRs, Fv, Fab and Fc fragments) or polymers of those immunoglobulin molecules and humanized versions of immunoglobulin molecules, as long as they exhibit any of the desired properties (e.g., specific binding of a gastric cancer, colorectal cancer and glioblastoma marker (poly)peptide, delivery of a toxin to a gastric cancer, colorectal cancer and glioblastoma cancer cell expressing a cancer marker gene at an increased level, and/or inhibiting the activity of a gastric cancer, colorectal cancer and glioblastoma cancer marker polypeptide) according to the description.

Whenever possible, the antibodies of the description may be purchased from commercial sources. The antibodies of the description may also be generated using well-known methods. The skilled artisan will understand that either full length non-small cell lung cancer marker polypeptides or fragments thereof may be used to generate the antibodies of the description. A polypeptide to be used for generating an antibody of the description may be partially or fully purified from a natural source, or may be produced using recombinant DNA techniques.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the description may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the description can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the description may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the description are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating non-small cell lung cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the description to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g., by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), domains recruiting effector cells such as an anti-CD3 domain, etc., in order to execute particular functions on target cells. In another aspect, it is expressed in T-cells used for adoptive transfer. See, for example, WO 2004/033685A1, WO 2004/074322A1, and WO 2013/057586A1, the contents of which are incorporated by reference in their entirety.

In addition, the peptides and/or the TCRs or antibodies or other binding molecules of the present description can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

The present invention will be further described in the following examples, nevertheless, without being limited thereto. For the purposes of the present invention, all references as cited herein are incorporated by reference in their entireties.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

EXAMPLES

HLA-Binding

The SYFPEITHI routine (Rammensee et al., 1997; Rammensee et al., 1999) predicts binding of KIQEILTQV (SEQ ID NO: 1) to A*02:01 with an absolute score of 27 and a relative score of 0.74. The peptide IGF2BP3-001 was presented on cancer cells as follows:

TABLE 4

| IGF2BP3-001 | CRC | GC | HCC | NSCLC | OC | OSCAR | PC | RCC |
|---|---|---|---|---|---|---|---|---|
| Natural presentation of IGF2BP3-001 peptide target (MS data) | | | | | | | | |
| Natural presentation directly shown on tumor samples | + | + | + | + | + | + | + | + |
| Presentation on normal tissues | Not detected on normal tissues (n = 241 samples) | | | | | | | |
| mRNA expression of IGF2BP3 source protein | | | | | | | | |
| Over-expressed on tumor samples (% of analyzed tumor samples) | 10 | 30 | 10 | 45 | 25 | 55 | 20 | 5 |
| Over-expression reported in the literature | + | + | + | + | + | + | + | + |

TABLE 4-continued

| IGF2BP3-001 | CRC GC HCC NSCLC OC OSCAR PC RCC |
|---|---|
| High and medium risk class normal tissues with highest expression (RPKM values median/Q95) | High risk: Lung (0.09/0.21)<br>Medium risk: Esophagus (0.47/1.85)<br>Low risk: Testis (1.89/3.2) |

| Immunogenicity and/or functional T-cell data |
|---|
| Immunogenic in a large fraction of tested A*02 positive donors (69%).<br>Primed T-cells are able to kill peptide-pulsed target cells. |

TABLE 5

Frequency of IGF2BP3-001 presentation

| A*02 | Samples | Mean intensity |
|---|---|---|
| Normal | 1 of 225 | — |
| Cancer | 63 of 376 | 7.5e+06 |
| cIPC | 9 of 20 | 1.9e+07 |
| CRC | 3 of 28 | 1.0e+07 |
| HCC | 7 of 16 | 1.2e+07 |
| OC | 7 of 20 | 6.4e+06 |
| OSCAR | 2 of 16 | 6.1e+06 |
| PC | 3 of 19 | 8.3e+06 |
| pCLL | 2 of 11 | 9.8e+06 |
| pCRC | 3 of 24 | 1.0e+07 |
| pGB | 5 of 28 | 5.6e+06 |
| pGC | 11 of 45 | 6.4e+06 |
| pNSCLC | 18 of 91 | 6.8e+06 |
| pPC | 3 of 18 | 8.3e+06 |
| pRCC | 3 of 18 | 1.4e+07 |
| RCC | 3 of 22 | 1.4e+07 |
| SCLC | 2 of 13 | 6.4e+06 |

Figure 1:
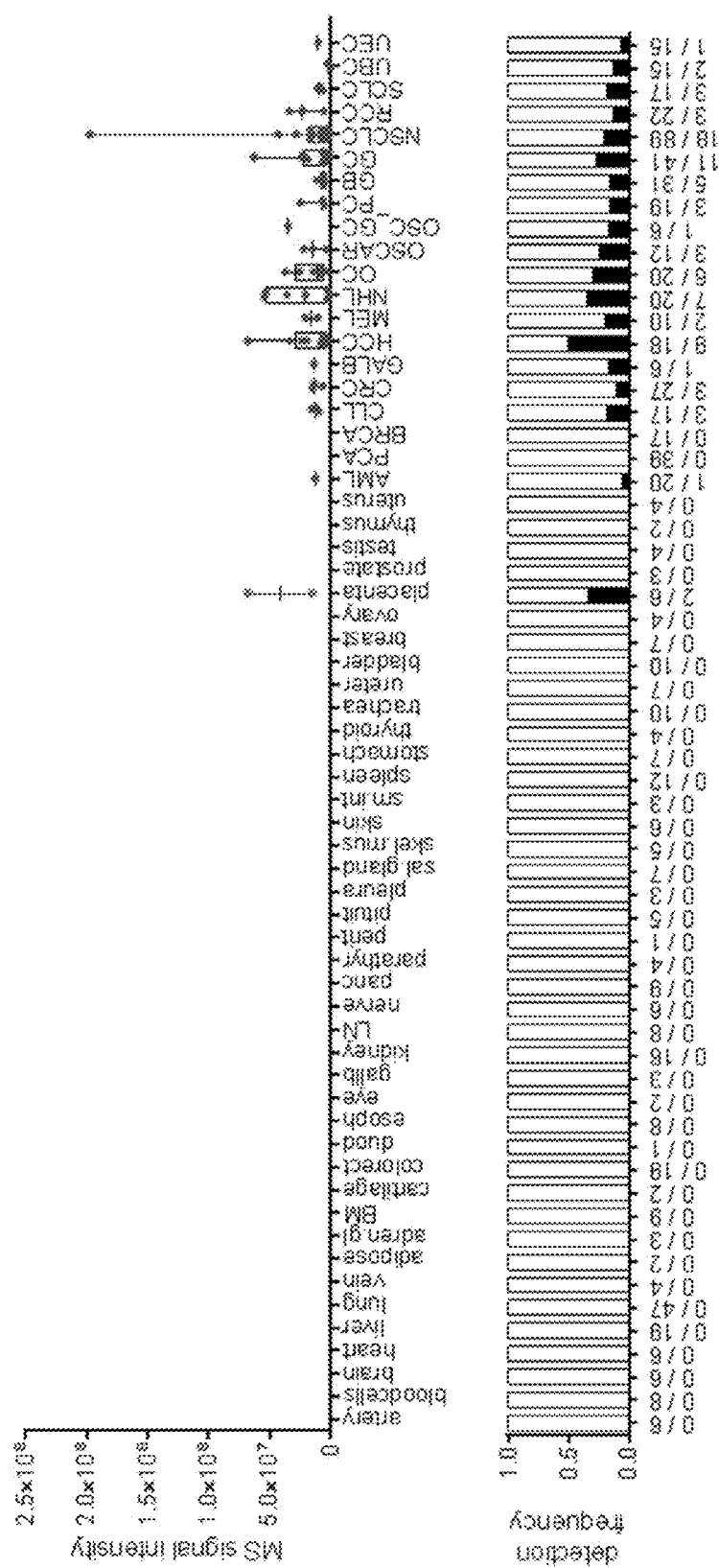
FIG. 1 shows IGF2BP3-001 peptide presentation in normal tissues and cancers.
Figure 2:
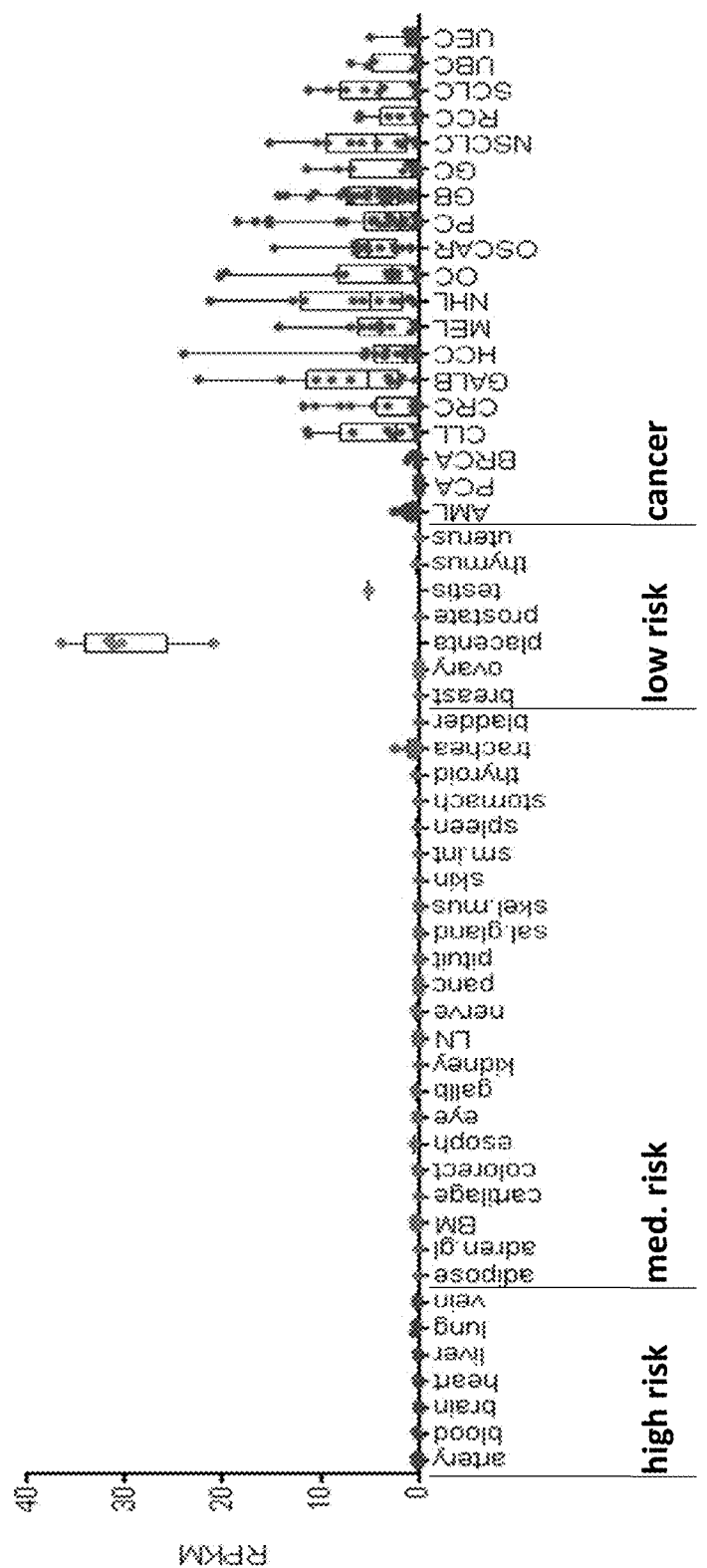
FIG. 2 shows IGF2BP3-001 expression in cancer and normal tissues.
Figure 3:
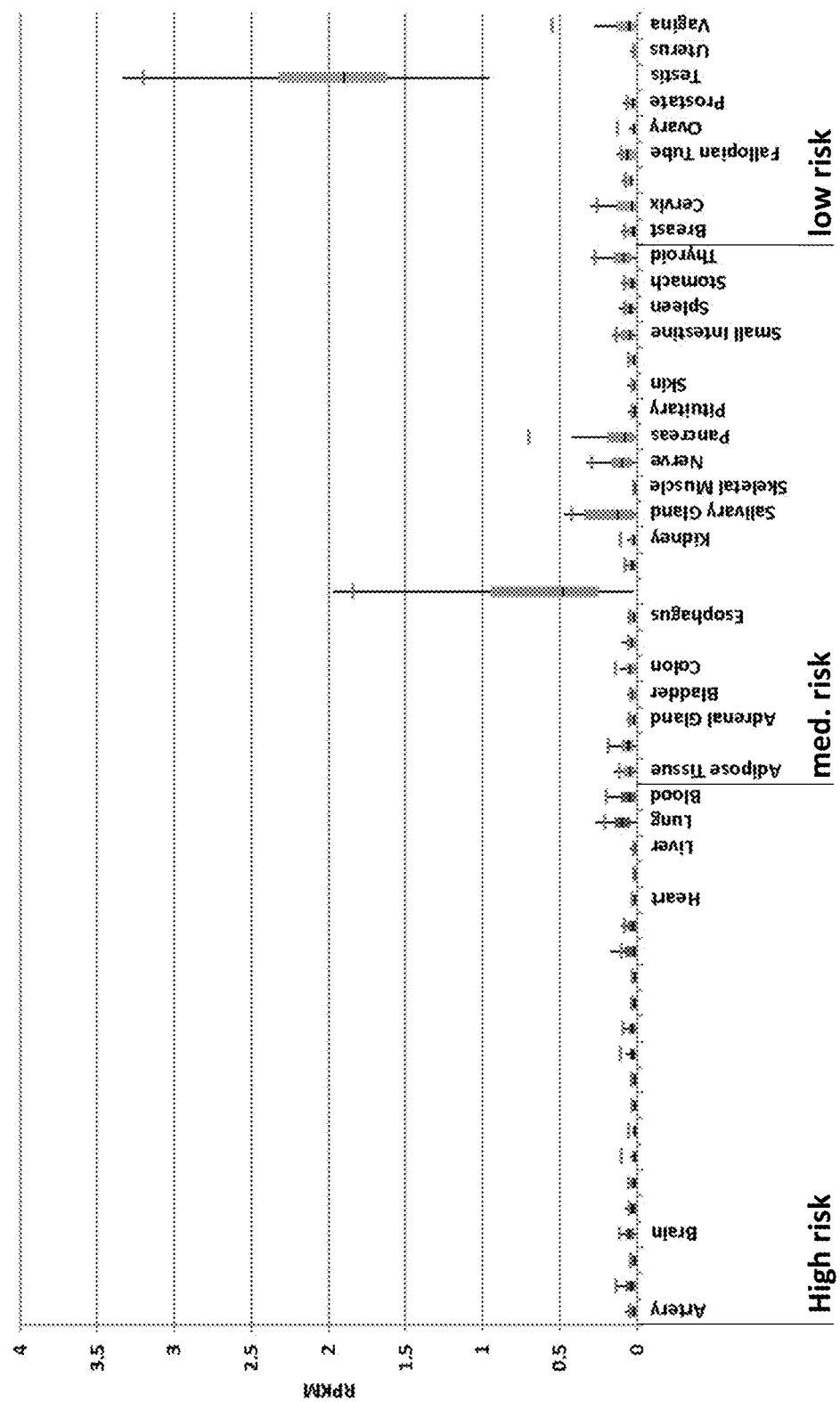
FIG. 3 shows IGF2BP3-001 expression in cancer and normal tissues.
Figure 4:
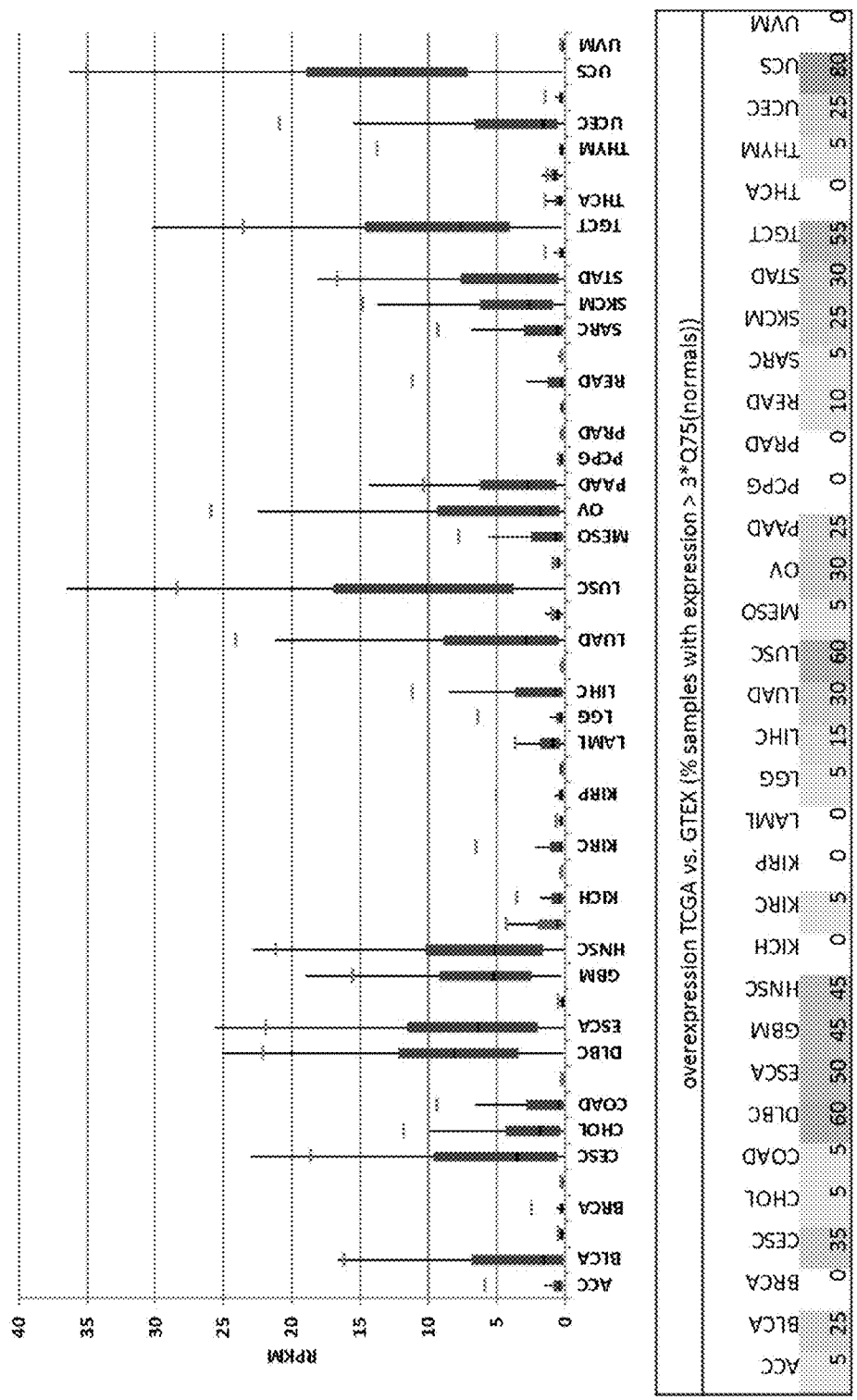
FIG. 4 shows IGF2BP3-001 expression in cancer and normal tissues.

IGF2BP3-001 was quantified in >380 HLA-A*02 positive tumor samples including 16 different cancer types and >240 normal tissue samples of different origin covering all risk categories with a focus on high and medium risk organs (status: August 2015). FIG. 1 shows the relative peptide presentation levels of IGF2BP3-001 in these tissues. IGF2BP3-001 was frequently and exclusively found on primary tumor samples of different entities and not on normal tissues. Thus, the IGF2BP3-001 target is presented in the context of HLA-A*02 in a highly tumor-specific manner.

Figure 5:
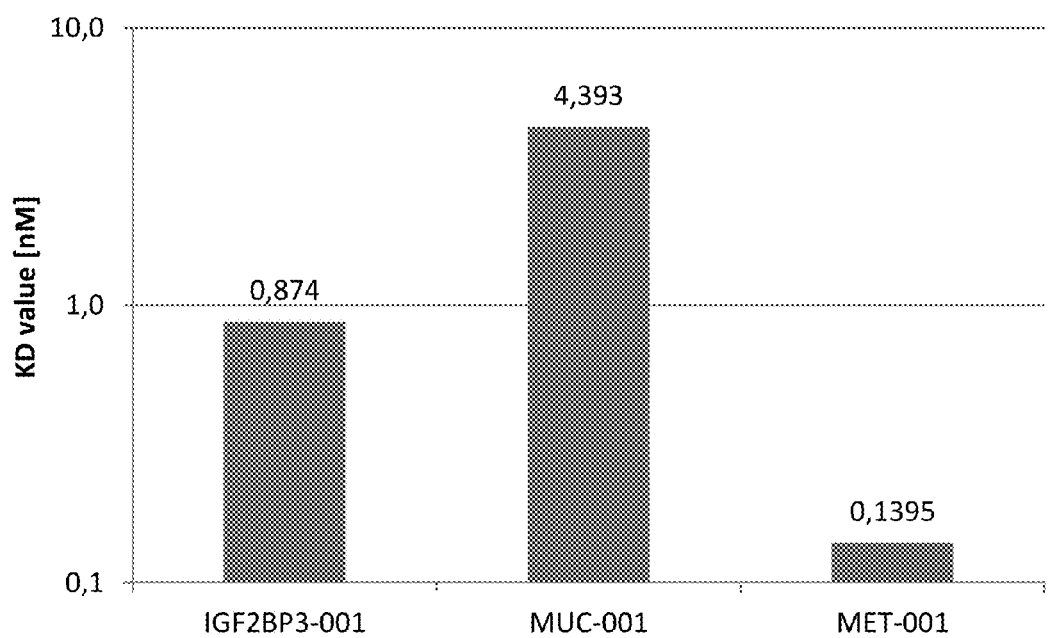
FIG. 5 shows affinities of IGF2BP3 to HLA-A*02:01 Dissociation constants (KD) of IGF2BP3 and control peptides MUC-001 (intermediate binder) and MET-001 (strong binder) were measured by an ELISA-based assay.

The data shown in FIG. 5 further provides evidence that IGF2BP3-001 is a peptide with very good binding to HLA-A*02:01.

Allo-reactive settings can be used to circumvent self-tolerance and yield T-cells with a higher avidity when compared to T-cells derived from autologous settings, i.e., patients. Examples of such settings include in vitro generation of allo-HLA reactive, peptide-specific T-cells (Sadovnikova et al. 1998; Savage et al. 2004; Wilde et al. 2012), and immunization of mice transgenic for human-MHC or human TCR (Stanislawski et al. 2001; Li et al. 2010).

Example 1

In vitro generation of allo-HLA reactive, peptide-specific T-cells (Savage et al. 2004) PBMCs from HLA-A*02-positive and HLA-A*02-negative healthy donors were used after obtaining informed consent. Recombinant biotinylated HLA-A2 class I monomers and A2 fluorescent tetramers containing IGF2BP3-001 were obtained from MBLI (Woburn, Mass.). PBMCs were incubated with anti-CD20SA diluted in phosphate buffered saline (PBS) for 1 hour at room temperature, washed, and incubated with the biotinylated A2/IGF2BP3-001 monomers for 30 minutes at room temperature, washed, and plated at $3 \times 10^6$ cells/well in 24-well plates in RPMI with 10% human AB serum. Interleukin 7 (IL-7; R&D Systems, Minneapolis, Minn.) was added on day 1 at 10 ng/mL and IL-2 (Chiron, Harefield, United Kingdom) was added at 10 U/mL on day 4. Over a 5-week period cells were restimulated weekly with fresh PBMCs, mixed with responder cells at a 1:1 ratio, and plated at $3 \times 10^6$/well in 24-well plates.

To obtain high avidity T-cells, approximately $10^6$ PBMCs with HLA-A2/IGF2BP3-001 tetramer-phycoerythrin (PE) (obtained from MBLI) were incubated for 30 minutes at 37° C., followed by anti-CD8-fluorescein isothiocyanate (FITC)/allophycocyanin (APC) for 20 minutes at 4° C., followed by fluorescence activated cell sorting (FACS)-Calibur analysis. Sorting was done with a FACS-Vantage (Becton Dickinson, Cowley, Oxford, United Kingdom). Sorted tetramer-positive cells were expanded in 24-well plates using, per well, $2 \times 10^5$ sorted cells, $2 \times 10^6$ irradiated A2-negative PBMCs as feeders, $2 \times 10^4$ CD3/CD28 beads/mL (Dynal, Oslo Norway), and IL-2 (1000 U/mL). The high avidity T-cells, thus obtained, were then used to identify and isolate TCRs using techniques known in the art, such as single cell 5' RACE (Rapid Amplification of cDNA Ends). Non-redundant TCR DNAs were then analyzed for amino acid/DNA sequences determination and cloning into expression vectors using methods well known in the art.

Example 2: Cloning of TCRs

Methods of cloning TCRs are known in the art, for example, as described in U.S. Pat. No. 8,519,100, which is hereby incorporated by reference in its entirety for said methods. The alpha chain variable region sequence specific oligonucleotide A1 (ggaattccatatgagtcaacaaggagaagaagatcc SEQ ID NO:11) which encodes the restriction site NdeI, an introduced methionine for efficient initiation of expression in bacteria, and an alpha chain constant region sequence specific oligonucleotide A2 (ttgtcagtcgacttagagtctctcagctgg-tacacg SEQ ID NO:12) which encodes the restriction site SalI are used to amplify the alpha chain variable region. In the case of the beta chain, a beta chain variable region sequence specific oligonucleotide B1 (tctctcatatggatggtg-gaattactcaatccccaa SEQ ID NO:13) which encodes the restriction site NdeI, an introduced methionine for efficient initiation of expression in bacteria, and a beta chain constant region sequence specific oligonucleotide B2 (tagaaaccggtg-gccaggcacaccagtgtggc SEQ ID NO:14) which encodes the restriction site AgeI are used to amplify the beta chain variable region.

Three TCRs (R10P1A7, R13P106, and R18P1C12), each encoding tumor specific TCR-alpha and TCR-beta chains, were isolated and cloned from T-cells of three healthy donors. TCR R18P1C12 was derived from HLA-A2 positive donor and TCR R10P1A7 and TCR R13P106 were derived from HLA-A2 negative donors.

The alpha and beta variable regions of the TCRs were sequenced. The TCR alpha and beta variable regions were then cloned into pGMT7-based expression plasmids containing either Cα or Cβ (respectively) by standard methods described in (Molecular Cloning a Laboratory Manual Third edition by Sambrook and Russell). Plasmids were sequenced using an Applied Biosystems 3730×1 DNA Analyzer.

The DNA sequences encoding the TCR alpha chain cut with NdeI and SalI were ligated into pGMT7+Cα vector, which was cut with NdeI and XhoI. The DNA sequences encoding the TCR beta chain cut with NdeI and AgeI was ligated into separate pGMT7+Cβ vector, which was also cut with NdeI and AgeI. Ligated plasmids are transformed into competent *Escherichia coli* strain XL1-blue cells and plated out on LB/agar plates containing 100 μg/ml ampicillin. Following incubation overnight at 37° C., single colonies are picked and grown in 10 ml LB containing 100 μg/ml ampicillin overnight at 37° C. with shaking. Cloned plasmids are purified using a Miniprep kit (Qiagen) and the insert is sequenced using an automated DNA sequencer (Lark Technologies).

Phage display can be used to generate libraries of TCR variants to identify high affinity mutants. The TCR phage display and screening methods described in (Li et al, (2005) Nature Biotech 23 (3): 349-354) can be applied to a reference TCR.

For example, all three CDR regions of the alpha chain sequence and all three CDR regions of the beta chain sequence can be targeted by mutagenesis, and each CDR library panned and screened separately.

Accordingly, TCRs with affinities and/or binding half-lives at least twice that of the reference TCR (and therefore impliedly at least twice that of the native TCR) can be identified.

TCR heterodimers are refolded using the method including the introduced cysteines in the constant regions to provide the artificial inter-chain disulphide bond. In that way TCRs are prepared, consisting of (a) the reference TCR beta chain, together with mutated alpha chains; (b) the reference TCR alpha chain together with mutated beta chains; and (c) various combinations of beta and alpha chains including the mutant variable domains.

The interaction between high affinity soluble disulfide-linked TCRs, and TCR variants, and the native peptide KIQEILTQV (SEQ ID NO: 1) HLA-A*02 complex can be analyzed using the BIAcore method.

High avidity TCR variants can also be selected from a library of CDR mutants by yeast, or T-cell display (Holler et al. 2003; Chervin et al. 2008). Candidate TCR variants, thus, provide guidance to design mutations of the TCR's CDRs to obtain high avidity TCR variants (Robbins et al. 2008; Zoete et al. 2007).

Example 3: Autologous T-Cell Engineering

T-cells can be engineered to express high avidity TCRs (so-called TCR therapies) or protein-fusion derived chimeric antigen receptors (CARs) that have enhanced antigen specificity to MHC I/IGF2BP3-001 complex or MHC II/IGF2BP3-001 complex. In an aspect, this approach overcomes some of the limitations associated with central and peripheral tolerance, and generate T-cells that will be more efficient at targeting tumors without the requirement for de novo T-cell activation in the patient.

In one aspect, to obtain T-cells expressing TCRs of the present description, nucleic acids encoding the tumor specific TCR-alpha and/or TCR-beta chains identified and isolated, as described in Examples 1-2, are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs were synthesized by techniques known in the art, e.g., in vitro transcription systems. The in vitro-synthesized TCR RNAs were then introduced into primary CD8+ T-cells obtained from healthy donors by electroporation to re-express tumor specific TCR-alpha and/or TCR-beta chains.

To test whether the exogenous TCRs were functionally expressed on cell surface of the transformed T-cells, a tetramer staining technique was used to detect MHC/IGF2BP3-001-binding T-cells. As shown in FIG. 5 and Table 6, a higher percentage of CD3-positive specific T-cell population, i.e., 6.78% (TCR R10P1A7) and 16.54% (TCR R13P106), was observed in TCR-expressing CD8+ T-cells by fluorescent-labeled MHC/IGF2BP3-001 tetramer staining than that with MHC/unrelated peptide (e.g., NYESO1-001) tetramers, e.g., 1.53%, or mock control, e.g., 1.73%. As a control, primary CD8+ T-cells transformed with unrelated TCRs, such as 1G4 TCR, which is known to bind specifically to MHC/NYESO1-001 complex, was readily detected by MHC/NYESO1-001 tetramer, i.e., 17.69%. These results indicate that TCR R10P1A7 and TCR R13P106 are expressed on T-cell surface and can bind specifically to MHC/IGF2BP3-001 complex.

To determine whether the TCRs induce MHC/IGF2BP3-001-specific cytotoxic activity, the transformed CD8+ T-cells were co-incubated with IGF2BP3-001-loaded target cells or with target cells loaded with similar but unrelated peptide, or with the controls, e.g., unloaded target cells and CD8+ T-cells only, followed by IFN-γ release assay. IFN-γ secretion from CD8+ T-cells is indicative of T-cell activation with cytotoxic activity.

TABLE 6

| TCR Code | Donor/HLA-A2 (+ or −) | IFNγ (pg/ml) | % specific TET in primary CD8+ T-cells | % TET IG4 control | EC50 |
|---|---|---|---|---|---|
| R10P1A7 | HBC-688/(−) | 175 | 6.78 | 1.53 | ~1 nM |
| R13P1C6 | HBC-686/(−) | 175-800 | 16.54 | 1.53 | ~0.8 nM |
| R18P1C12 | na/(+) | 25-75 | 3.64 | 1.53 | na |

It was found that all primary CD8+ T-cells transformed with TCRs of the present disclosure, after co-incubation with IGF2BP3-001-loaded target cells, released much higher levels of IFN-γ than that stimulated by unrelated peptide-loaded target cells, and the controls. Target peptide titration analysis showed EC50 at ~1 nM (TCR R10P1A7) and ~0.8 nM (TCR R13P106). These results suggest that TCRs of the present invention can activate cytotoxic T-cell activity, e.g., IFN-γ release, through specific interaction with the MHC/IGF2BP3-001 complex.

To determine the binding motif of the TCRs for the MHC/IGF2BP3-001 complex, positional alanine scanning analysis was performed at each of the 9 amino acids of the IGF2BP3-001 peptide. Alanine-substituted IGF2BP3-001 peptides are shown in Table 7.

TABLE 7

|  | Position: | | | | | | | | |
| --- | --- | --- | --- | --- | --- | --- | --- | --- | --- |
|  | 1 | 2 | 3 | 4 | 5 | 6 | 7 | 8 | 9 |
| IGF2BP3-001 (SEQ ID NO: 1) | K | I | Q | E | I | L | T | Q | V |
| IGF2BP3-001 A1 (SEQ ID NO: 19) | A | I | Q | E | I | L | T | Q | V |
| IGF2BP3-001 A2 (SEQ ID NO: 20) | K | A | Q | E | I | L | T | Q | V |
| IGF2BP3-001 A3 (SEQ ID NO: 21) | K | I | A | E | I | L | T | Q | V |
| IGF2BP3-001 A4 (SEQ ID NO: 22) | K | I | Q | A | I | L | T | Q | V |
| IGF2BP3-001 A5 (SEQ ID NO: 23) | K | I | Q | E | A | L | T | Q | V |
| IGF2BP3-001 A6 (SEQ ID NO: 24) | K | I | Q | E | I | A | T | Q | V |
| IGF2BP3-001 A7 (SEQ ID NO: 25) | K | I | Q | E | I | L | A | Q | V |
| IGF2BP3-001 A8 (SEQ ID NO: 26) | K | I | Q | E | I | L | T | A | V |
| IGF2BP3-001 A9 (SEQ ID NO: 27) | K | I | Q | E | I | L | T | Q | A |

Briefly, T-cells transformed with each TCR were co-incubated with target cells loaded with IGF2BP3-001, IGF2BP3-001-A1 to IGF2BP3-001-A9, or an unrelated NYESO1-001 peptide, followed by IFNγ release assay, as described above.

Results of positional alanine scanning analysis on TCR R10P1A7 and TCR R13P106 are summarized in Table 8.

TABLE 8

| TCR | IGF2BP3-001 positions enable TCR binding |
| --- | --- |
| R10P1A7 | 1, 3-7 |
| R13P1C6 | 3-6 |

A genome-wide screen for A*02-binding peptides with an identical motif revealed no potentially cross-reactive peptides. These results suggest that IGF2BP3-001 positions 3-6 may be important for TCR R10P1A7 and TCR R13P106 binding.

To determine efficacy of T-cells expressing TCRs described herein, primary CD8+ T-cells transformed with TCR R10P1A7 were co-incubated with human cancer cell lines, e.g., A-375 (human melanoma cell line) and T98G (human glioblastoma cell line), which are HLA-A2-positive and IGF2BP3-001 (target)-positive, and SK-BR-3 (human breast cancer cell line), which is HLA-A2-negative and IGF2BP3-001-negative, followed by IFNγ release assay.

IFNγ release was observed in both A-375 and T98G cells, which are HLA-A2-positive and IGF2BP3-001-positive, but not in SK-BR-3 cells, which have basal levels of IFNγ release that is comparable to that of effector cell only control. These results indicate that T-cells expressing TCR R10P1A7 can specifically induce cytotoxic activity targeting cancer cells in a HLA-A2/IGF2BP3-001 specific manner.

The present description provides TCRs that are useful in treating cancers/tumors, preferably melanoma and glioblastoma that over- or exclusively present IGF2BP3-001.

Example 4: Allogeneic T-Cell Engineering

Gamma delta (γδ) T cells, which are non-conventional T lymphocyte effectors implicated in the first line of defense against pathogens, can interact with and eradicate tumor cells in a MHC-independent manner through activating receptors, among others, TCR-gamma and TCR-delta chains. These γδ T cells display a preactivated phenotype that allows rapid cytokine production (IFN-γ, TNF-α) and strong cytotoxic response upon activation. These T-cells have anti-tumor activity against many cancers and suggest that γδ T cell-mediated immunotherapy is feasible and can induce objective tumor responses. (Braza et al. 2013).

Recent advances using immobilized antigens, agonistic monoclonal antibodies (mAbs), tumor-derived artificial antigen presenting cells (aAPC), or combinations of activating mAbs and aAPC have been successful in expanding gamma delta T-cells with oligoclonal or polyclonal TCR repertoires. For example, immobilized major histocompatibility complex Class-I chain-related A was a stimulus for γδ T-cells expressing TCRδ1 isotypes, and plate-bound activating antibodies have expanded Vδ1 and Vδ2 cells ex vivo. Clinically sufficient quantities of TCRδ1, TCRδ2, and TCRδ1$^{neg}$TCRδ2$^{neg}$ have been produced following co-culture on aAPC, and these subsets displayed differences in memory phenotype and reactivity to tumors in vitro and in vivo. (Deniger et al. 2014).

In addition, γδ T-cells are amenable to genetic modification as evidenced by introduction of TCR-alpha and TCR-beta chains. (Hiasa et al. 2009). Another aspect of the present description relates to production of γδ T-cells expressing TCR-alpha and TCR-beta that bind to IGF2BP3-001. To do so, γδ T-cells are expanded by methods described by Deniger et al. 2014, followed by transducing the recombinant viruses expressing the TCRs that bind to IGF2BP3-001 (as described in Example 3) into the expanded γδ T-cells. The virus-transduced γδ T-cells are then infused into the patient.

Example 5: mRNA Expression

In situ hybridization (ISH) was used to detect mRNA expression directly in formalin-fixed or frozen tissue sections. Due to its high sensitivity and its spatial resolution, it is a suitable method to determine cell type specific target expression and the distribution or frequency of target expression within cancer tissue sections.

ISH has been performed to detect IGF2BP3 mRNA using the RNAscope® technology developed by Advanced Cell Diagnostics (ACD). The RNAscope® technology is based on the hybridization of around 20 pairs of Z-shaped oligonucleotide probes to the target sequence. Signal amplification is achieved by branched DNA amplification, which is based on multiple hybridization steps of oligonucleotides, ultimately building up a branched DNA (bDNA) tree. Finally, a great number of label probes hybridize to the branches of the bDNA tree and the enhanced signal can be detected. The chromogenic RNAscope® Detection Kit (RED) includes label probes which are linked to an enzyme (alkaline phosphatase). Signal detection depends on the enzymatic conversion of the chromogenic substrate FastRed, which additionally amplifies the original signal. RNAscope® is a very sensitive technology, which is due to the efficient process of signal amplification, paired with the high sensitivity and the robust binding of the Z probe pairs to the target mRNA, even if it is partially crosslinked or degraded. According to ACD, binding of three out of 20 probe pairs to each single RNA molecule is enough to generate a detectable ISH signal.

Each ISH experiment is subdivided into two methodological processes: 1) Tissue pretreatment for target retrieval, and 2) Target hybridization, signal amplification and detection. Optimal pretreatment conditions are critical for successful target detection in FFPE tissue sections. The fixation process induces crosslinking of proteins, DNA and RNA in cells and tissues and thereby masks hybridization sites. Thus, to assure accessibility of the target mRNA and proper binding of the probe set, these crosslinks have to be removed prior to target hybridization. Tissue pretreatment includes three discrete steps: 1) Blocking of endogenous alkaline phosphatase by hydrogen peroxide treatment, 2) target retrieval by boiling in target retrieval reagent, and 3) target retrieval by protease digestion. As the extent of fixation and crosslinking may vary between different FFPE blocks, the optimal target retrieval conditions have to be determined experimentally for each individual FFPE block. Therefore, tissue sections were exposed to different boiling and protease digestion times followed by hybridization with a positive and a negative control probe set. The optimal conditions were determined by microscopic evaluation of specific signal intensity in the positive control, unspecific background in the negative control and tissue morphology. Tissue pretreatment was performed according to the manufacturer's protocols. Pretreatment reagents are included in the RNAscope® reagent kits. After completion of the different pretreatment steps, target expression was assessed by hybridization of specific probe sets to the mRNA of interest with subsequent branched DNA signal amplification and chromogenic or fluorescent signal detection. All assays were performed according to the manufacturer's protocols.

Figure 6:
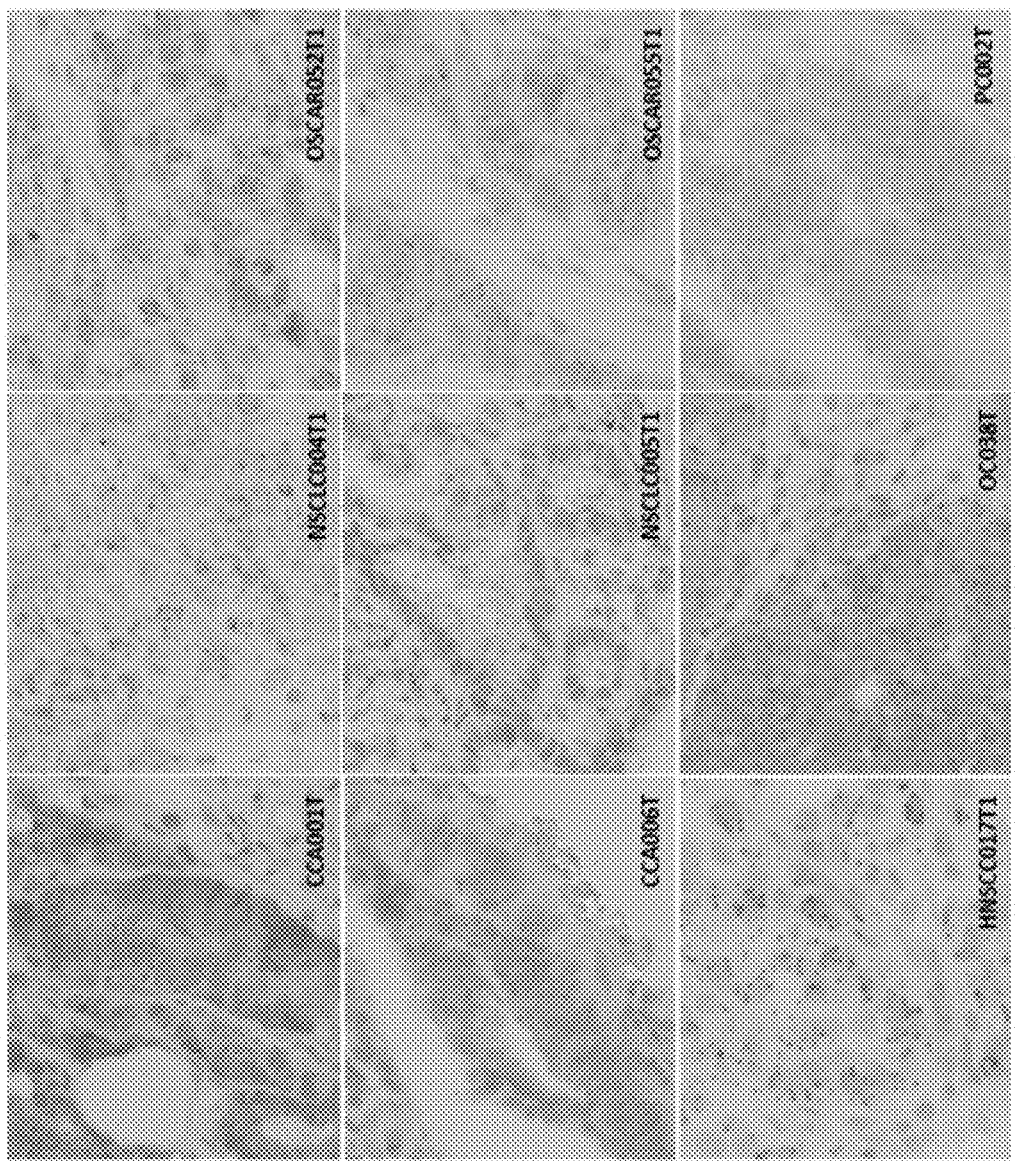
FIG. 6 shows that IGF2BP3 mRNA is detectable in all evaluated cancer specimens as in Example 6. The level of expression covers a range from considerable expression in colorectal cancer, head and neck cancer, non-small cell lung cancer, ovarian cancer and esophageal cancer specimens (CCA001T, CCA006T, HNSCC017T1, NSCLC004T1, NSCLC005T1, 00038T, OSCAR052T1 and OSCAR055T1) to rather low expression in a pancreatic cancer specimen (PC002T).

TABLE 9 mRNA expression (see FIG. 6)

| Sample | Tissue | IGF2BP3 expression |
|---|---|---|
| CCA001T | Colorectal cancer | ++ |
| CCA006T | Colorectal cancer | ++ |
| HNSCC017T1 | Head and neck cancer | ++ |
| NSCLC004T1 | Non-small cell lung cancer | ++ |
| NSCLC005T1 | Non-small cell lung cancer | ++ |
| OC038T1 | Ovarian cancer | ++ |
| OSCAR052T1 | Esophageal cancer | ++ |
| OSCAR055T1 | Esophageal cancer | ++ |
| PC002T | Pancreatic cancer | + |

Overall expression level of IGF2BP3 in the respective section: ± very low, + low to moderate, ++ strong, +++ very strong

REFERENCE LIST

Brossart P, Bevan M J. Presentation of exogenous protein antigens on major histocompatibility complex class I molecules by dendritic cells: pathway of presentation and regulation by cytokines. Blood. 1997 Aug. 15; 90(4): 1594-9.

Gnjatic S, Atanackovic D, Jäger E, Matsuo M, Selvakumar A, Altorki N K, Maki R G, Dupont B, Ritter G, Chen Y T, Knuth A, Old L J. Survey of naturally occurring CD4+ T cell responses against NY-ESO-1 in cancer patients: correlation with antibody responses. Proc Natl Acad Sci USA. 2003 Jul. 22; 100(15):8862-7.

Mortara L, Castellani P, Meazza R, Tosi G, De Lerma Barbaro A, Procopio F A, Comes A, Zardi L, Ferrini S, Accolla R S. CIITA-induced MHC class II expression in mammary adenocarcinoma leads to a Th1 polarization of the tumor microenvironment, tumor rejection, and specific antitumor memory. Clin Cancer Res. 2006 Jun. 1; 12(11 Pt 1):3435-43.

Dengjel J, Nastke M D, Gouttefangeas C, Gitsioudis G, Schoor O, Altenberend F, Müller M, Kramer B, Missiou A, Sauter M, Hennenlotter J, Wernet D, Stenzl A, Rammensee H G, Klingel K, Stevanović S. Unexpected abundance of HLA class II presented peptides in primary renal cell carcinomas. Clin Cancer Res. 2006 Jul. 15; 12(14 Pt 1):4163-70.

Tran E, Turcotte S, Gros A, Robbins P F, Lu Y C, Dudley M E, Wunderlich J R, Somerville R P, Hogan K, Hinrichs C S, Parkhurst M R, Yang J C, Rosenberg S A. Cancer immunotherapy based on mutation-specific CD4+ T cells in a patient with epithelial cancer. Science. 2014 May 9; 344(6184):641-5.

Singh-Jasuja H, Emmerich N P, Rammensee H G. The Tübingen approach: identification, selection, and validation of tumor-associated HLA peptides for cancer therapy. Cancer Immunol Immunother. 2004 March; 53(3):187-95. Epub 2004 Jan. 31. Review.

Mori M, Beatty P G, Graves M, Boucher K M, Milford E L. HLA gene and haplotype frequencies in the North American population: the National Marrow Donor Program Donor Registry. Transplantation. 1997 Oct. 15; 64(7): 1017-27.

Colombetti S, Fagerberg T, Baumgärtner P, Chapatte L, Speiser D E, Rufer N, Michielin O, Lévy F. Impact of orthologous melan-A peptide immunizations on the anti-self melan-A/HLA-A2 T cell cross-reactivity. J Immunol. 2006 Jun. 1; 176(11):6560-7.

Appay V, Speiser D E, Rufer N, Reynard S, Barbey C, Cerottini J C, Leyvraz S, Pinilla C, Romero P. Decreased specific CD8+ T cell cross-reactivity of antigen recognition following vaccination with Melan-A peptide. Eur J Immunol. 2006 July; 36(7):1805-14.

Xing Y, Hogquist K A. T-cell tolerance: central and peripheral. Cold Spring Harb Perspect Biol. 2012 Jun. 1; 4(6).

Aleksic M, Liddy N, Molloy P E, Pumphrey N, Vuidepot A, Chang K M, Jakobsen B K. Different affinity windows for virus and cancer-specific T-cell receptors: implications for therapeutic strategies. Eur J Immunol. 2012 December; 42(12):3174-9.

Burton E C, Prados M D. Malignant gliomas. Curr Treat Options Oncol. 2000 December; 1(5):459-68. Review.

Dutoit V, Herold-Mende C, Hilf N, Schoor O, Beckhove P, Bucher J, Dorsch K, Flohr S, Fritsche J, Lewandrowski P, Lohr J, Rammensee H G, Stevanovic S, Trautwein C, Vass V, Walter S, Walker P R, Weinschenk T, Singh-Jasuja H, Dietrich P Y. Exploiting the glioblastoma peptidome to discover novel tumour-associated antigens for immunotherapy. Brain. 2012 April; 135(Pt 4):1042-54.

Tomita, Y., Harao, M., Senju, S., Imai, K., Hirata, S., Irie, A., Inoue, M., Hayashida, Y., Yoshimoto, K., Shiraishi, K., Mori, T., Nomori, H., Kohrogi, H. and Nishimura, Y. (2011), Peptides derived from human insulin-like growth factor-II mRNA binding protein 3 can induce human leukocyte antigen-A2-restricted cytotoxic T lymphocytes reactive to cancer cells. Cancer Science, 102: 71-78.

Barton V N, Donson A M, Birks D K, Kleinschmidt-DeMasters B K, Handler M H, Foreman N K, Rush S Z (2013). Insulin-like growth factor 2 mRNA binding protein 3 expression is an independent prognostic factor in pediatric pilocytic and pilomyxoid astrocytoma. J Neuropathol. Exp. Neurol. 72, 442-449.

Beljan P R, Durdov M G, Capkun V, Ivcevic V, Pavlovic A, Soljic V, Peric M (2012). IMP3 can predict aggressive behaviour of lung adenocarcinoma. Diagn. Pathol. 7, 165.

Bell J L, Wachter K, Muhleck B, Pazaitis N, Kohn M, Lederer M, Huttelmaier S (2013). Insulin-like growth factor 2 mRNA-binding proteins (IGF2BPs): post-transcriptional drivers of cancer progression? Cell Mol. Life Sci. 70, 2657-2675.

Chen C L, Tsukamoto H, Liu J C, Kashiwabara C, Feldman D, Sher L, Dooley S, French S W, Mishra L, Petrovic L, Jeong J H, Machida K (2013a). Reciprocal regulation by TLR4 and TGF-beta in tumor-initiating stem-like cells. J Clin Invest 123, 2832-2849.

Chen L T, Lin L J, Zheng L L (2013b). The correlation between insulin-like growth factor II mRNA binding protein 3 expression in hepatocellular carcinoma and prognosis. Hepatogastroenterology 60, 553-556.

Chen P, Wang S J, Wang H B, Ren P, Wang X Q, Liu W G, Gu W L, Li D Q, Zhang T G, Zhou C J (2012). The distribution of IGF2 and IMP3 in osteosarcoma and its relationship with angiogenesis. J Mol. Histol. 43, 63-70.

Chen S T, Jeng Y M, Chang C C, Chang H H, Huang M C, Juan H F, Hsu C H, Lee H, Liao Y F, Lee Y L, Hsu W M, Lai H S (2011). Insulin-like growth factor II mRNA-binding protein 3 expression predicts unfavorable prognosis in patients with neuroblastoma. Cancer Sci. 102, 2191-2198.

Chen Y L, Jeng Y M, Hsu H C, Lai H S, Lee P H, Lai P L, Yuan R H (2013c). Expression of insulin-like growth factor II mRNA-binding protein 3 predicts early recurrence and poor prognosis in intrahepatic cholangiocarcinoma. Int. J Surg. 11, 85-91.

Chiste M, Alexis J, Recine M (2014). IMP3 expression in serous tumors of the ovary. Appl. Immunohistochem. Mol. Morphol. 22, 658-662.

Del G A, Vaira V, Rocco E G, Palleschi A, Bulfamante G, Ricca D, Fiori S, Bosari S, Ferrero S (2014). The Oncofetal Protein IMP3: A Useful Marker to Predict Poor Clinical Outcome in Neuroendocrine Tumors of the Lung. J Thorac. Oncol.

Eldai H, Periyasamy S, Al Q S, Al R M, Muhammed M S, Deeb A, Al S E, Afzal M, Johani M, Yousef Z, Aziz M A (2013). Novel genes associated with colorectal cancer are revealed by high resolution cytogenetic analysis in a patient specific manner. PLoS. ONE. 8, e76251.

Feng W, Zhou Z, Peters J H, Khoury T, Zhai Q, Wei Q, Truong C D, Song S W, Tan D (2011). Expression of insulin-like growth factor II mRNA-binding protein 3 in human esophageal adenocarcinoma and its precursor lesions. Arch. Pathol. Lab Med. 135, 1024-1031.

Findeis-Hosey J J, Xu H (2012). Insulin-like growth factor II-messenger RNA-binding protein-3 and lung cancer. Biotech. Histochem. 87, 24-29.

Gu L, Shigemasa K, Ohama K (2004). Increased expression of IGF II mRNA-binding protein 1 mRNA is associated with an advanced clinical stage and poor prognosis in patients with ovarian cancer. Int. J Oncol 24, 671-678.

Hammer N A, Hansen T, Byskov A G, Rajpert-De M E, Grondahl M L, Bredkjaer H E, Wewer U M, Christiansen J, Nielsen F C (2005). Expression of IGF-II mRNA-binding proteins (IMPs) in gonads and testicular cancer. Reproduction. 130, 203-212.

Hazama S, Nakamura Y, Takenouchi H, Suzuki N, Tsunedomi R, Inoue Y, Tokuhisa Y, Iizuka N, Yoshino S, Takeda K, Shinozaki H, Kamiya A, Furukawa H, Oka M (2014). A phase I study of combination vaccine treatment of five therapeutic epitope-peptides for metastatic colorectal cancer; safety, immunological response, and clinical outcome. J Transl. Med. 12, 63.

Hoffmann N E, Sheinin Y, Lohse C M, Parker A S, Leibovich B C, Jiang Z, Kwon E D (2008). External validation of IMP3 expression as an independent prognostic marker for metastatic progression and death for patients with clear cell renal cell carcinoma. Cancer 112, 1471-1479.

Hu S, Wu X, Zhou B, Xu Z, Qin J, Lu H, Lv L, Gao Y, Deng L, Yin J, Li G (2014). IMP3 combined with CD44s, a novel predictor for prognosis of patients with hepatocellular carcinoma. J Cancer Res Clin Oncol 140, 883-893.

Hwang Y S, Park K K, Cha I H, Kim J, Chung W Y (2012a). Role of insulin-like growth factor-II mRNA-binding protein-3 in invadopodia formation and the growth of oral squamous cell carcinoma in athymic nude mice. Head Neck 34, 1329-1339.

Hwang Y S, Xianglan Z, Park K K, Chung W Y (2012b). Functional invadopodia formation through stabilization of the PDPN transcript by IMP-3 and cancer-stromal crosstalk for PDPN expression. Carcinogenesis 33, 2135-2146.

Iinuma H, Fukushima R, Inaba T, Tamura J, Inoue T, Ogawa E, Horikawa M, Ikeda Y, Matsutani N, Takeda K, Yoshida K, Tsunoda T, Ikeda T, Nakamura Y, Okinaga K (2014). Phase I clinical study of multiple epitope peptide vaccine combined with chemoradiation therapy in esophageal cancer patients. J Transl. Med. 12, 84.

Ikenberg K, Fritzsche F R, Zuerrer-Haerdi U, Hofmann I, Hermanns T, Seifert H, Muntener M, Provenzano M, Sulser T, Behnke S, Gerhardt J, Mortezavi A, Wild P, Hofstadter F, Burger M, Moch H, Kristiansen G (2010). Insulin-like growth factor II mRNA binding protein 3 (IMP3) is overexpressed in prostate cancer and correlates with higher Gleason scores. BMC. Cancer 10, 341.

Jeng Y M, Chang C C, Hu F C, Chou H Y, Kao H L, Wang T H, Hsu H C (2008). RNA-binding protein insulin-like growth factor II mRNA-binding protein 3 expression promotes tumor invasion and predicts early recurrence and poor prognosis in hepatocellular carcinoma. Hepatology 48, 1118-1127.

Jeng Y M, Wang T H, Lu S H, Yuan R H, Hsu H C (2009). Prognostic significance of insulin-like growth factor II mRNA-binding protein 3 expression in gastric adenocarcinoma. Br. J Surg 96, 66-73.

Jin L, Seys A R, Zhang S, Erickson-Johnson M R, Roth C W, Evers B R, Oliveira A M, Lloyd R V (2010). Diagnostic utility of IMP3 expression in thyroid neoplasms: a quantitative R T-PCR study. Diagn. Mol. Pathol. 19, 63-69.

Kazeminezhad B, Mirafsharieh S A, Dinyari K, Azizi D, Ebrahimi A (2014). Usefulness of insulin-like growth factor II mRNA-binding protein 3 (IMP3) as a new marker for the diagnosis of esophageal adenocarcinoma in challenging cases. Turk. J Gastroenterol. 25, 253-256.

Kleinschmidt-DeMasters B K, Donson A M, Vogel H, Foreman N K (2014). Pilomyxoid Astrocytoma (PMA) Shows Significant Differences in Gene Expression vs. Pilocytic Astrocytoma (P A) and Variable Tendency Toward Maturation to PA. Brain Pathol.

Kobel M, Xu H, Bourne P A, Spaulding B O, Shih I, Mao T L, Soslow R A, Ewanowich C A, Kalloger S E, Mehl E, Lee C H, Huntsman D, Gilks C B (2009). IGF2BP3 (IMP3) expression is a marker of unfavorable prognosis in ovarian carcinoma of clear cell subtype. Mod. Pathol. 22, 469-475.

Kono K, Iinuma H, Akutsu Y, Tanaka H, Hayashi N, Uchikado Y, Noguchi T, Fujii H, Okinaka K, Fukushima R, Matsubara H, Ohira M, Baba H, Natsugoe S, Kitano S, Takeda K, Yoshida K, Tsunoda T, Nakamura Y (2012). Multicenter, phase II clinical trial of cancer vaccination for advanced esophageal cancer with three peptides derived from novel cancer-testis antigens. J Transl. Med. 10, 141.

Kono K, Mizukami Y, Daigo Y, Takano A, Masuda K, Yoshida K, Tsunoda T, Kawaguchi Y, Nakamura Y, Fujii H (2009). Vaccination with multiple peptides derived from novel cancer-testis antigens can induce specific T-cell responses and clinical responses in advanced esophageal cancer. Cancer Sci. 100, 1502-1509.

Li D, Yan D, Tang H, Zhou C, Fan J, Li S, Wang X, Xia J, Huang F, Qiu G, Peng Z (2009). IMP3 is a novel prognostic marker that correlates with colon cancer progression and pathogenesis. Ann Surg Oncol 16, 3499-3506.

Li H G, Han J J, Huang Z Q, Wang L, Chen W L, Shen X M (2011). IMP3 is a novel biomarker to predict metastasis and prognosis of tongue squamous cell carcinoma. J Craniofac. Surg. 22, 2022-2025.

Liao B, Hu Y, Brewer G (2011). RNA-binding protein insulin-like growth factor mRNA-binding protein 3 (IMP-3) promotes cell survival via insulin-like growth factor II signaling after ionizing radiation. J Biol. Chem. 286, 31145-31152.

Liao B, Hu Y, Herrick D J, Brewer G (2005). The RNA-binding protein IMP-3 is a translational activator of insulin-like growth factor II leader-3 mRNA during proliferation of human K562 leukemia cells. J Biol. Chem. 280, 18517-18524.

Lin L, Zhang J, Wang Y, Ju W, Ma Y, Li L, Chen L (2013). Insulin-like growth factor-II mRNA-binding protein 3 predicts a poor prognosis for colorectal adenocarcinoma. Oncol Lett. 6, 740-744.

Liu H, Shi J, Anandan V, Wang H L, Diehl D, Blansfield J, Gerhard G, Lin F (2012). Reevaluation and identification of the best immunohistochemical panel (pVHL, Maspin, S100P, IMP-3) for ductal adenocarcinoma of the pancreas. Arch. Pathol. Lab Med. 136, 601-609.

Lochhead P, Imamura Y, Morikawa T, Kuchiba A, Yamauchi M, Liao X, Qian Z R, Nishihara R, Wu K, Meyerhardt J A, Fuchs C S, Ogino S (2012). Insulin-like growth factor 2 messenger RNA binding protein 3 (IGF2BP3) is a marker of unfavourable prognosis in colorectal cancer. Eur. J Cancer.

Lu D, Vohra P, Chu P G, Woda B, Rock K L, Jiang Z (2009). An oncofetal protein IMP3: a new molecular marker for the detection of esophageal adenocarcinoma and high-grade dysplasia. Am J Surg Pathol. 33, 521-525.

Lu D, Yang X, Jiang N Y, Woda B A, Liu Q, Dresser K, Mercurio A M, Rock K L, Jiang Z (2011). IMP3, a new biomarker to predict progression of cervical intraepithelial neoplasia into invasive cancer. Am. J Surg. Pathol. 35, 1638-1645.

Mizukami Y, Kono K, Daigo Y, Takano A, Tsunoda T, Kawaguchi Y, Nakamura Y, Fujii H (2008). Detection of novel cancer-testis antigen-specific T-cell responses in TIL, regional lymph nodes, and PBL in patients with esophageal squamous cell carcinoma. Cancer Sci.

Morimatsu K, Aishima S, Yamamoto H, Hayashi A, Nakata K, Oda Y, Shindo K, Fujino M, Tanaka M, Oda Y (2013). Insulin-like growth factor II messenger RNA-binding protein-3 is a valuable diagnostic and prognostic marker of intraductal papillary mucinous neoplasm. Hum. Pathol. 44, 1714-1721.

Nielsen J, Christiansen J, Lykke-Andersen J, Johnsen A H, Wewer U M, Nielsen F C (1999). A family of insulin-like growth factor II mRNA-binding proteins represses translation in late development. Mol Cell Biol. 19, 1262-1270.

Noske A, Faggad A, Wirtz R, Darb-Esfahani S, Sehouli J, Sinn B, Nielsen F C, Weichert W, Buckendahl A C, Roske A, Muller B, Dietel M, Denkert C (2009). IMP3 expression in human ovarian cancer is associated with improved survival. Int. J Gynecol. Pathol. 28, 203-210.

Okada K, Fujiwara Y, Nakamura Y, Takiguchi S, Nakajima K, Miyata H, Yamasaki M, Kurokawa Y, Takahashi T, Mori M, Doki Y (2012). Oncofetal protein, IMP-3, a potential marker for prediction of postoperative peritoneal dissemination in gastric adenocarcinoma. J Surg. Oncol 105, 780-785.

Pryor J G, Bourne P A, Yang Q, Spaulding B O, Scott G A, Xu H (2008). IMP-3 is a novel progression marker in malignant melanoma. Mod. Pathol. 21, 431-437.

Rammensee H G, Bachmann J, Emmerich N P, Bachor O A, Stevanovic S (1999). SYFPEITHI: database for MHC ligands and peptide motifs. Immunogenetics 50, 213-219.

Rammensee H G, Bachmann J, Stevanovic S (1997). MHC Ligands and Peptide Motifs. (Heidelberg, Germany: Springer-Verlag).

Rivera V T, Boudoukha S, Simon A, Souidi M, Cuvellier S, Pinna G, Polesskaya A (2013). Post-transcriptional regulation of cyclins D1, D3 and G1 and proliferation of human cancer cells depend on IMP-3 nuclear localization. Oncogene.

Samanta S, Sharma V M, Khan A, Mercurio A M (2012). Regulation of IMP3 by EGFR signaling and repression by ERbeta: implications for triple-negative breast cancer. Oncogene 31, 4689-4697.

Samanta S, Sun H, Goel H L, Pursell B, Chang C, Khan A, Greiner D L, Cao S, Lim E, Shultz L D, Mercurio A M (2015). IMP3 promotes stem-like properties in triple-negative breast cancer by regulating SLUG. Oncogene.

Schaeffer D F, Owen D R, Lim H J, Buczkowski A K, Chung S W, Scudamore C H, Huntsman D G, Ng S S, Owen D A (2010). Insulin-like growth factor 2 mRNA binding protein 3 (IGF2BP3) overexpression in pancreatic ductal adenocarcinoma correlates with poor survival. BMC. Cancer 10, 59.

Serao N V, Delfino K R, Southey B R, Beever J E, Rodriguez-Zas S L (2011). Cell cycle and aging, morphogenesis, and response to stimuli genes are individualized biomarkers of glioblastoma progression and survival. BMC. Med. Genomics 4, 49.

Su P, Hu J, Zhang H, Li W, Jia M, Zhang X, Wu X, Cheng H, Xiang L, Zhou G (2014). IMP3 expression is associated with epithelial-mesenchymal transition in breast cancer. Int. J Clin Exp. Pathol. 7, 3008-3017.

Suda T, Tsunoda T, Daigo Y, Nakamura Y, Tahara H (2007). Identification of human leukocyte antigen-A24-restricted epitope peptides derived from gene products upregulated in lung and esophageal cancers as novel targets for immunotherapy. Cancer Sci.

Suvasini R, Shruti B, Thota B, Shinde S V, Friedmann-Morvinski D, Nawaz Z, Prasanna K V, Thennarasu K, Hegde A S, Arivazhagan A, Chandramouli B A, Santosh V, Somasundaram K (2011). Insulin growth factor-2 binding protein 3 (IGF2BP3) is a glioblastoma-specific marker that activates phosphatidylinositol 3-kinase/mitogen-activated protein kinase (PI3K/MAPK) pathways by modulating IGF-2. J Biol. Chem. 286, 25882-25890.

Szarvas T, Tschirdewahn S, Niedworok C, Kramer G, Sevcenco S, Reis H, Shariat S F, Rubben H, Vom D F (2014). Prognostic value of tissue and circulating levels of IMP3 in prostate cancer. Int. J Cancer 135, 1596-1604.

Takata A, Takiguchi S, Okada K, Takahashi T, Kurokawa Y, Yamasaki M, Miyata H, Nakajima K, Mori M, Doki Y (2014). Expression of insulin-like growth factor-II mRNA-binding protein-3 as a marker for predicting clinical outcome in patients with esophageal squamous cell carcinoma. Oncol Lett. 8, 2027-2031.

Taniuchi K, Furihata M, Hanazaki K, Saito M, Saibara T (2014). IGF2BP3-mediated translation in cell protrusions promotes cell invasiveness and metastasis of pancreatic cancer. Oncotarget. 5, 6832-6845.

Tomita Y, Harao M, Senju S, Imai K, Hirata S, Irie A, Inoue M, Hayashida Y, Yoshimoto K, Shiraishi K, Mori T, Nomori H, Kohrogi H, Nishimura Y (2011). Peptides derived from human insulin-like growth factor-II mRNA binding protein 3 can induce human leukocyte antigen-A2-restricted cytotoxic T lymphocytes reactive to cancer cells. Cancer Sci. 102, 71-78.

Ueki A, Shimizu T, Masuda K, Yamaguchi S I, Ishikawa T, Sugihara E, Onishi N, Kuninaka S, Miyoshi K, Muto A, Toyama Y, Banno K, Aoki D, Saya H (2012). Up-regulation of Imp3 confers in vivo tumorigenicity on murine osteosarcoma cells. PLoS. ONE. 7, e50621.

Vikesaa J, Hansen T V, Jonson L, Borup R, Wewer U M, Christiansen J, Nielsen F C (2006). RNA-binding IMPs promote cell adhesion and invadopodia formation. EMBO J 25, 1456-1468.

Wachter D L, Kristiansen G, Soil C, Hellerbrand C, Breuhahn K, Fritzsche F, Agaimy A, Hartmann A, Riener M O (2012). Insulin-like growth factor II mRNA-binding protein 3 (IMP3) expression in hepatocellular carcinoma. A clinicopathological analysis with emphasis on diagnostic value. Histopathology 60, 278-286.

Wachter D L, Schlabrakowski A, Hoegel J, Kristiansen G, Hartmann A, Riener M O (2011). Diagnostic value of immunohistochemical IMP3 expression in core needle biopsies of pancreatic ductal adenocarcinoma. Am. J Surg. Pathol. 35, 873-877.

Wang B J, Wang L, Yang S Y, Liu Z J (2015). Expression and clinical significance of IMP3 in microdissected premalignant and malignant pancreatic lesions. Clin Transl. Oncol 17, 215-222.

Wang L, Li H G, Xia Z S, Lu J, Peng T S (2010). IMP3 is a novel biomarker to predict metastasis and prognosis of gastric adenocarcinoma: a retrospective study. Chin Med. J (Engl.) 123, 3554-3558.

Wang Y, Li L, Wang Y, Yuan Z, Zhang W, Hatch K D, Zheng W (2014). IMP3 as a cytoplasmic biomarker for early serous tubal carcinogenesis. J Exp. Clin Cancer Res. 33, Yantiss R K, Cosar E, Fischer A H (2008). Use of IMP3 in identification of carcinoma in fine needle aspiration biopsies of pancreas. Acta Cytol. 52, 133-138.

Yoshino K, Motoyama S, Koyota S, Shibuya K, Sato Y, Sasaki T, Wakita A, Saito H, Minamiya Y, Sugiyama T, Ogawa J (2014). Identification of insulin-like growth factor 2 mRNA-binding protein 3 as a radioresistance factor in squamous esophageal cancer cells. Dis. Esophagus. 27, 479-484.

Yuan R, Chen Y, He X, Wu X, Ke J, Zou Y, Cai Z, Zeng Y, Wang L, Wang J, Fan X, Wu X, Lan P (2013). CCL18 as an independent favorable prognostic biomarker in patients with colorectal cancer. J Surg. Res 183, 163-169.

Yuan R H, Wang C C, Chou C C, Chang K J, Lee P H, Jeng Y M (2009). Diffuse expression of RNA-binding protein IMP3 predicts high-stage lymph node metastasis and poor prognosis in colorectal adenocarcinoma. Ann Surg Oncol 16, 1711-1719.

Zhang Y, Garcia-Buitrago M T, Koru-Sengul T, Schuman S, Ganjei-Azar P (2013). An immunohistochemical panel to distinguish ovarian from uterine serous papillary carcinomas. Int. J Gynecol. Pathol. 32, 476-481.

---

The invention claimed is:

1. A method of eliciting an immune response in a patient who has cancer, comprising administering to the patient a composition comprising a population of activated T cells that selectively recognize the cancer cells that present a peptide consisting of the amino acid sequence of KIQEILTQV (SEQ ID NO: 1),
wherein the activated T cells are produced by contacting T cells with the peptide loaded human class I or II MHC molecules expressed on the surface of an antigen-presenting cell for a period of time sufficient to activate the T cells,
wherein said cancer is selected from the group consisting of oral carcinomas, *H. pylori*-induced MALT lymphoma, Ewing's sarcoma, head and neck squamous cell carcinoma, epithelial cancer of the larynx, carcinoma of the urinary bladder, atypical meningioma, papillary thyroid carcinoma, salivary duct carcinoma, cervical cancer, extranodal T/NK-cell lymphomas, and non-Hodgkin's lymphoma.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 1, wherein the peptide is in a complex with the class I MHC molecule.

7. The method of claim 1, wherein the antigen presenting cell is infected with recombinant virus expressing the peptide.

8. The method of claim 7, wherein the antigen presenting cell is a dendritic cell or a macrophage.

9. The method of claim 5, wherein the expansion is in the presence of an anti-CD28 antibody and IL-2.

10. The method of claim 1, wherein the population of activated T cells comprises CD8-positive cells.

11. The method of claim 1, wherein the contacting is in vitro.

12. The method of claim 1, wherein the composition further comprises an adjuvant.

13. The method of claim 12, wherein the adjuvant is selected from the group consisting of anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

14. The method of claim 1, wherein the immune response comprises a cytotoxic T cell response.

15. A method of killing cancer cells, comprising eliciting the immune response of claim 1.

16. The method of claim 15, wherein the immune response comprises a cytotoxic T cell response.

17. The method of claim 1, wherein the cancer is cervical cancer.

18. The method of claim 1, wherein the cancer is head and neck squamous cell carcinoma.

19. The method of claim 1, wherein the cancer is non-Hodgkin's lymphoma.

20. A method of eliciting an immune response in a patient who has oral carcinomas, *H. pylori*-induced MALT lymphoma, Ewing's sarcoma, head and neck squamous cell carcinoma, epithelial cancer of the larynx, carcinoma of the urinary bladder, atypical meningioma, papillary thyroid carcinoma, salivary duct carcinoma, cervical cancer, extranodal T/NK-cell lymphomas, and/or non-Hodgkin's lymphoma, comprising administering to said patient a composition comprising a peptide in the form of a pharmaceutically acceptable salt, wherein said peptide consists of the amino acid sequence of KIQEILTQV (SEQ ID NO: 1), thereby inducing a T-cell response to the oral carcinomas, *H. pylori*-induced MALT lymphoma, Ewing's sarcoma, head and neck squamous cell carcinoma, epithelial cancer of the larynx, carcinoma of the urinary bladder, atypical meningioma, papillary thyroid carcinoma, salivary duct carcinoma, cervical cancer, extranodal T/NK-cell lymphomas, and/or non-Hodgkin's lymphoma.

21. The method of claim 1, wherein the cancer is carcinoma of the urinary bladder.

22. The method of claim 20, wherein the patient has carcinoma of the urinary bladder.

\* \* \* \* \*

SEQUENCE LISTING

```
<160> NUMBER OF SEQ ID NOS: 14

<210> SEQ ID NO 1
<211> LENGTH: 9
<212> TYPE: PRT
<213> ORGANISM: Homo sapiens

<400> SEQUENCE: 1

Lys Ile Gln Glu Ile Leu Thr Gln Val
1               5

<210> SEQ ID NO 2
<211> LENGTH: 9
<212> TYPE: PRT
<213> ORGANISM: Homo sapiens

<400> SEQUENCE: 2

Ala Ile Gln Glu Ile Leu Thr Gln Val
1               5

<210> SEQ ID NO 3
<211> LENGTH: 9
<212> TYPE: PRT
<213> ORGANISM: Homo sapiens

<400> SEQUENCE: 3

Lys Ala Gln Glu Ile Leu Thr Gln Val
1               5

<210> SEQ ID NO 4
```

```
<211> LENGTH: 9
<212> TYPE: PRT
<213> ORGANISM: Homo sapiens

<400> SEQUENCE: 4

Lys Ile Ala Glu Ile Leu Thr Gln Val
1               5

<210> SEQ ID NO 5
<211> LENGTH: 9
<212> TYPE: PRT
<213> ORGANISM: Homo sapiens

<400> SEQUENCE: 5

Lys Ile Gln Ala Ile Leu Thr Gln Val
1               5

<210> SEQ ID NO 6
<211> LENGTH: 9
<212> TYPE: PRT
<213> ORGANISM: Homo sapiens

<400> SEQUENCE: 6

Lys Ile Gln Glu Ala Leu Thr Gln Val
1               5

<210> SEQ ID NO 7
<211> LENGTH: 9
<212> TYPE: PRT
<213> ORGANISM: Homo sapiens

<400> SEQUENCE: 7

Lys Ile Gln Glu Ile Ala Thr Gln Val
1               5

<210> SEQ ID NO 8
<211> LENGTH: 9
<212> TYPE: PRT
<213> ORGANISM: Homo sapiens

<400> SEQUENCE: 8

Lys Ile Gln Glu Ile Leu Ala Gln Val
1               5

<210> SEQ ID NO 9
<211> LENGTH: 9
<212> TYPE: PRT
<213> ORGANISM: Homo sapiens

<400> SEQUENCE: 9

Lys Ile Gln Glu Ile Leu Thr Ala Val
1               5

<210> SEQ ID NO 10
<211> LENGTH: 9
<212> TYPE: PRT
<213> ORGANISM: Homo sapiens

<400> SEQUENCE: 10

Lys Ile Gln Glu Ile Leu Thr Gln Ala
1               5

<210> SEQ ID NO 11
<211> LENGTH: 36
<212> TYPE: DNA
```

```
<213> ORGANISM: Homo sapiens

<400> SEQUENCE: 11
ggaattccat atgagtcaac aaggagaaga agatcc                              36

<210> SEQ ID NO 12
<211> LENGTH: 36
<212> TYPE: DNA
<213> ORGANISM: Homo sapiens

<400> SEQUENCE: 12
ttgtcagtcg acttagagtc tctcagctgg tacacg                              36

<210> SEQ ID NO 13
<211> LENGTH: 36
<212> TYPE: DNA
<213> ORGANISM: Homo sapiens

<400> SEQUENCE: 13
tctctcatat ggatggtgga attactcaat ccccaa                              36

<210> SEQ ID NO 14
<211> LENGTH: 32
<212> TYPE: DNA
<213> ORGANISM: Homo sapiens

<400> SEQUENCE: 14
tagaaaccgg tggccaggca caccagtgtg gc                                  32
```